(12) United States Patent
Zayed et al.

(10) Patent No.: US 11,169,145 B2
(45) Date of Patent: Nov. 9, 2021

(54) METHODS OF DETECTION AND TREATMENT FOR CARDIOVASCULAR DISEASE AND FOOT WOUNDS

(71) Applicants: Mohamed Zayed, St. Louis, MO (US); Clay Semenkovich, St. Louis, MO (US)

(72) Inventors: Mohamed Zayed, St. Louis, MO (US); Clay Semenkovich, St. Louis, MO (US)

(73) Assignee: Washington University, St. Louis, MO (US)

( * ) Notice: Subject to any disclaimer, the term of this patent is extended or adjusted under 35 U.S.C. 154(b) by 92 days.

(21) Appl. No.: 15/967,719

(22) Filed: May 1, 2018

(65) Prior Publication Data

US 2018/0321225 A1 Nov. 8, 2018

Related U.S. Application Data

(60) Provisional application No. 62/492,447, filed on May 1, 2017.

(51) Int. Cl.
| | |
|---|---|
| *G01N 33/50* | (2006.01) |
| *G01N 33/49* | (2006.01) |
| *G01N 33/573* | (2006.01) |
| *G01N 33/68* | (2006.01) |
| *G01N 33/92* | (2006.01) |
| *A61K 31/444* | (2006.01) |

(52) U.S. Cl.
CPC ....... *G01N 33/5091* (2013.01); *G01N 33/492* (2013.01); *G01N 33/573* (2013.01); *G01N 33/6893* (2013.01); *G01N 33/92* (2013.01); *A61K 31/444* (2013.01); *C12Y 203/01085* (2013.01); *G01N 2333/32* (2013.01); *G01N 2333/91057* (2013.01); *G01N 2800/042* (2013.01); *G01N 2800/324* (2013.01); *G01N 2800/325* (2013.01); *G01N 2800/326* (2013.01); *G01N 2800/327* (2013.01); *G01N 2800/328* (2013.01); *G01N 2800/52* (2013.01); *G01N 2800/56* (2013.01)

(58) Field of Classification Search
CPC ............. G01N 33/5091; G01N 33/492; G01N 33/573; G01N 33/6893; G01N 33/92; G01N 2333/32; G01N 2333/91057; G01N 2800/042; G01N 2800/324; G01N 2800/325; G01N 2800/326; G01N 2800/327; G01N 2800/328; G01N 2800/52; G01N 2800/56; A61K 31/444; C12Y 203/01085
See application file for complete search history.

(56) References Cited

U.S. PATENT DOCUMENTS

| | | | | |
|---|---|---|---|---|
| 2009/0162870 A1* | 6/2009 | Medghalchi | ......... | G01N 33/573 435/7.4 |
| 2012/0165218 A1* | 6/2012 | Muraca | ............ | G01N 33/57434 506/9 |

FOREIGN PATENT DOCUMENTS

| | | | | |
|---|---|---|---|---|
| WO | WO2002/00855 | 3/2002 | | |
| WO | WO2009/64927 | 5/2009 | | |
| WO | WO2013/123305 | 8/2013 | | |
| WO | WO2013/188605 | 12/2013 | | |
| WO | WO-2013188605 A2 * | 12/2013 | ........... | C12Q 1/6883 |
| WO | WO2015/026893 | 2/2015 | | |

OTHER PUBLICATIONS

Bai, N., Mouse Study Reveals Mechanism behind Diabetes Blood Vessel Damage, 2011, Scientific American, https://www.scientificamerican.com/article/diabetes-blood-vessel-damage/ (Year: 2011).*
Schneider et. al., Macrophage Fatty-acid Synthase Deficiency Decreases Diet-induced Atherosclerosis, 2010, The Journal of Biological Chemistry, 285(30), 23398-23409 (Year: 2010).*
Gibbons et. al., Diabetic Vascular Disease: Characteristics of Vascular Disease Unique to the Diabetic Patient, 2012, Seminars in Vascular Surgery, 25,89-92 (Year: 2012).*
De Franciscis et. al., Cilostazol prevents foot ulcers in diabetic patients with peripheral vascular disease, 2015, International Wound Journal, 12, 250-253 (Year: 2015).*
Olin, J. et. al., Peripheral Artery Disease: Current Insight Into the Disease and Its Diagnosis and Management, 2010, May Clinic Proceedings, 85(7), 678-692 (Year: 2010).*
Bays, N. et al., A Simplified Scintillation Proximity Assay for Fatty Acid Synthase Activity: Development and Comparison with Other FAS Activity Assays, 2009, Journal of Biomolecular Screening, 636-642 (Year: 2009).*
Abbott et al. (1988)—The impact of diabetes on survival following myocardial infarction in men versus women: The Framingham Study, Jama, 260, pp. 3456-3460.
Alkhaldi et al. (2015)—The Effectiveness of Technology-Based Strategies to Promote Engagement with Digital Interventions: A Systematic Review Protocol, JMIR Research Protocols, 4, 2, pp. e47.

(Continued)

*Primary Examiner* — Louise W Humphrey
*Assistant Examiner* — Anjali Ajit Hirani

(57) ABSTRACT

Among the various aspects of the present disclosure is the provision of a method of detection, treatment, and monitoring of cardiovascular disease or a foot wound by detection of a novel biomarker, Fatty Acid Synthase (FAS). Briefly, therefore, the present disclosure is directed to methods that allow for improved, noninvasive, and reliable diagnosis of these conditions, particularly in subjects suffering from Type 2 Diabetes (T2D).

23 Claims, 13 Drawing Sheets

(56) References Cited

OTHER PUBLICATIONS

Alla et al. (2016)—Inhibition of G-protein-coupled Receptor Kinase 2 Prevents the Dysfunctional Cardiac Substrate Metabolism in Fatty Acid Synthase Transgenic Mice, The Journal of biological chemistry, 29, 6, pp. 2583-2600.
American Diabetes Association (1999)—Consensus Development Conference on Diabetic Foot Wound Care: Apr. 7-8, 1999, Boston, Massachusetts. American Diabetes Association, Diabetes care, 22, 8, pp. 1354-1360.
Apelqvist et al. (2011)—Factors related to outcome of neuroischemic/ischemic foot ulcer in diabetic patients, Journal of Vascular Surgery, 53, 6, pp. 1582-1588.
Armstrong et al. (1998)—Choosing a practical screening instrument to identify patients at risk for diabetic foot ulceration, Arch. Intern. Med., 158, 3, pp. 289-292.
Arora et al. (2002)—Cutaneous microcirculation in the neuropathic diabetic foot improves significantly but not completely after successful lower extremity revascularization, Journal of Vascular Surgery, 35, 3, pp. 501-505.
Arsenault et al. (2011)—The use of transcutaneous oximetry to predict complications of chronic wound healing: A systematic review and meta-analysis, Wound Repairand Regeneration, 19, 6, pp. 657-663.
Asal, Wojciak (2017)—Effect of cilostazol in treating diabetes-associated microvascular complications, Endocrine, 56, 2, pp. 240-244.
Bauer et al. (2007)—Skeletal Muscle Deoxygenation After the Slowed Microvascular Blood Flow Kinetics, Diabetes care, 30,11, pp. 2880-2885.
Beckman, Creager, Libby (2002)—Diabetes and Atherosclerosis Epidemiology, Pathophysiology, and Management, JAMA, 287, 19, pp. 2570-2581.
Berndt et al. (2007)—Fatty acid synthase gene expression in human adipose tissue: Association with obesity and type 2 diabetes, Diabetologia, 50, 7, pp. 1472-1480.
Bohannon, Wang, Gershon (2015)—Two-minute walk test performance by adults 18 to 85 years: Normative values, reliability, and responsiveness, Archives of Physical Medicine and Rehabilitation, 96, 3, pp. 472-477.
Boulton et al. (2005)—The global burden of diabetic foot disease, Lancet, 366, 9498, pp. 1719-1724.
Boyko et al. (1996)—Predictors of transcutaneous oxygen tension in the lower limbs of diabetic subjects, Diabetic Medicine, 13, 6, pp. 549-554.
Boyle et al. (2010)—Projection of the year 2050 burden of diabetes in the US adult population: Dynamic modeling of incidence, mortality, and prediabetes prevalence, Population Health Metrics, 8, 29, pp. 1-12.
Brooks et al. (2001)—The 2-minute walk test as a measure of functional improvement in persons with lower limb amputation, Archives of Physical Medicine and Rehabilitation, 82, 10, pp. 1478-1483.
Caselli et al. (2005)—Transcutaneous oxygen tension monitoring after successful revascularization in diabetic patients with ischaemic foot ulcers, Diabetic Medicine, 22, 4, pp. 460-465.
CDC Diabetes in Managed Care Work Group (2001)—Diabetes mellitus in managed care: Complications and resource utilization, American Journal of Managed Care, 7, 5, pp. 501-508.
Centers for Disease Control and Prevention (2017)—National Diabetes Statistics Report, 2017: Estimates of Diabetes and Its Burden in the Epidemiologic estimation methods, US Department of Health and Human Services, pp. 1-20.
Chao, Cheing (2009)—Microvascular dysfunction in diabetic foot disease and ulceration, Diabetes/Metabolism Research and Reviews, 25, pp. 604-614.
Clarke et al. (2004)—A model to estimate the lifetime health outcomes of patients with Type 2 diabetes: The United Kingdom Prospective Diabetes Study (UKPDS) Outcomes Model (UKPDS No. 68). Diabetologia, 47, 10, pp. 1747-1759.
Cobb, Claremont (2002)—Noninvasive Measurement Techniques for Monitoring of Microvascular Function in the Diabetic Foot, Lower Extremity Wounds, 1, 3, pp. 161-169.
Commean et al. (2002)—Reliability and validity of combined imaging and pressures assessment methods for diabetic feet, Archives of Physical Medicine and Rehabilitation, 83, 4, pp. 497-505.
Corpeleijn et al. (2006)—Improvements in glucose tolerance and insulin sensitivity after lifestyle intervention are related to changes in serum fatty acid profile and desaturase activities: the SLIM study, Diabetologia, 49, 10, pp. 2392-2401.
Cruz et al. (2014)—Colonic Mucosal Fatty Acid Synthase as an Early Biomarker for Colorectal Neoplasia: Modulation by Obesity and Gender, Cancer Epidemiol Biomarkers Prev., 23, 11, pp. 2413-2421.
Dawson et al. (1998)—Cilostazol Has Beneficial Effects in Treatment of Intermittent Claudication, Circulation, 98, pp. 678-686.
De Franciscis et al. (2015)—Cilostazol prevents foot ulcers in diabetic patients with peripheral vascular disease, International Wound Journal, 12, 3, pp. 250-253.
Dinh, Veves (2005)—Microcirculation of the diabetic foot, Current pharmaceutical design, 11, 18, pp. 2301-2309.
Elraiyah et al. (2016)—A systematic review and meta-analysis of adjunctive therapies in diabetic foot ulcers, Journal of Vascular Surgery, 63, 2, pp. 46S-58S.
Eneroth, Larsson, Apelqvist (1999)—Deep Foot Infections in Patients with Diabetes and Foot Ulcer: An Entity with and Prognosis Different Characteristics, Treatments, Journal of Diabetes and its Complications, 13, 5-6, pp. 254-263.
Erkkilä et al. (2008)—Dietary fatty acids and cardiovascular disease: An epidemiological approach, Progress in Lipid Research, 47, 3, pp. 172-187.
Fernandez-Real et al. (2010)—Extracellular Fatty Acid Synthase: A Possible Surrogate Biomarker of Insulin Resistance, Diabetes, 59, pp. 1506-1511.
Forsythe, Brownrigg, Hinchliffe (2015)—Peripheral arterial disease and revascularization of the diabetic foot, Diabetes Obes. Metab., 17, 5, pp. 435-444.
Forsythe, Hinchliffe (2016)—Assessment of foot perfusion in patients with a diabetic foot ulcer, Diabetes/Metabolism Research and Reviews, 32, Suppl. 1, pp. 232-238.
Gabarron et al. (2012)—Avatars using computer/smartphone mediated communication and social networking in prevention of sexually transmitted diseases among North-Norwegian youngsters, BMC Medical Informatics and Decision Making, 12, 120, pp. 1-5.
Geng et al. (2012)—Effect of cilostazol on the progression of carotid intima-media thickness: A meta-analysis of randomized controlled trials, Atherosclerosis, 220, 1, pp. 177-183.
Greenman et al. (2005)—Early changes in the skin microcirculation and muscle metabolism of the diabetic foot, Lancet (London, England), 366, 9498, pp. 1711-1717.
Gregg et al. (2014)—Changes in Diabetes-Related Complications in the United States, 1990-2010, New England Journal of Medicine, 370, 16, pp. 1514-1523.
Grunfeld (1992)—Diabetic foot ulcers: Etiology, treatment, and prevention, Advances in Internal Medicine, 37, pp. 103-132.
Hastings et al. (2012)—Botulinum toxin effects on gasatrocnemius strength and plantar pressure in diabetics with peripheral neuropathy and forefoot ulceration, Foot Ankle Int., 33, 5, pp. 363-370.
Herman, Kahn (2012)—Adipose tissue de novo lipogenesis. Unanticipated benefits in health and disease, ASBMB today, February, pp. 30-32. Accessed on Nov. 21, 2017 at http://www.asbmb.org/asbmbtoday/asbmbtoday_article.aspx?id=15872 (3 pages).
HHS: U.S. Department of Health and Human Services et al. (2006)—Guidance for industry: chronic cutaneous ulcer and burn wounds-developing products for treatment., Clinical/Medical, June, pp. 1-18.
Hilton et al. (2008)—Excessive Adipose Tissue Infiltration in Skeletal Muscle in Individuals with Obesity, Diabetes Mellitus, and Peripheral Neuropathy: Association With Performance and Function, Physical Therapy, 88, 11, pp. 1336-1344.

(56) References Cited

OTHER PUBLICATIONS

Hodson, Skeaff, Fielding (2008)—Fatty acid composition of adipose tissue and blood in humans and its use as a biomarker of dietary intake, Progress in Lipid Research, 47, 5, pp. 348-380.
Ijzerman et al. (2012)—Lower extremity muscle strength is reduced in people with type 2 diabetes, with and without polyneuropathy, and is associated with impaired mobility and reduced quality of life, Diabetes Research and Clinical Practice, 95, 3, pp. 345-351.
Itoh et al. (2003)—Free fatty acids regulate insulin secretion from pancreatic beta cells through GPR40, Nature Medicine, 422, pp. 173-176.
Jensen-Urstad, Semenkovich (2012)—Fatty acid synthase and liver triglyceride metabolism: Housekeeper or messenger? Biochimica et Biophysica Acta—Molecular and Cell Biology of Lipids, 1821, 5, pp. 747-753.
Katakami et al. (2010)—The phosphodiesterase inhibitor cilostazol induces regression of carotid atherosclerosis in subjects with type 2 diabetes mellitus: Principal results of the diabetic atherosclerosis prevention by cilostazol (DAPC) study: A randomized trial, Circulation, 121, 23, pp. 2584-2591.
Kirchhoff et al. (2012)—Breast cancer risk and 6q22.33: Combined results from breast cancer association consortium and consortium of investigators on modifiers of brca1/2, PLoS ONE, 7, 6, e35706.
Krishnan et al. (2004)—Comparative roles of microvascular and nerve function in foot ulceration in type 2 diabetes, Diabetes Care, 27, 6, pp. 1343-1348.
Kumar et al. (2013)—Mobile health technology evaluation: The mHealth evidence workshop, American Journal of Preventive Medicine, 45, 2, pp. 228-236.
Ladurner et al. (2010)—Predictive value of routine transcutaneous tissue oxygen tension (tcpO2) measurement for the risk of non-healing and amputation in diabetic foot ulcer patients with non-palpable pedal pulses., Medical science monitor, 16, 6, pp. CR273-CR277.
Lindley et al. (2016)—Biology and biomarkers for wound healing, Plastic and Reconstructive Surgery, 138, 3, pp. 18S-28S.
Lovejoy et al. (2002)—Effects of Diets Enriched in Saturated (Palmitic), Monounsaturated (Oleic), or trans (Elaidic) Fatty Acids on Insulin Sensitivity and Substrate Oxidation in Healthy Adults, Diabetes Care, 25, 8, pp. 1283-1288.
Madigan et al. (2014)—Novel nuclear localization of fatty acid synthase correlates with prostate cancer aggressiveness, American Journal of Pathology, 184, 8, pp. 2156-2162.
Malik et al. (1989)—Microangiopathy in human diabetic neuropathy: relationship between capillary abnormalities and the severity of neuropathy, Diabetologia, 32, pp. 92-102.
Mccommis et al. (2010)—Quantification of Regional Myocardial Oxygenation by Magnetic Resonance Imaging: Validation with Positron Emission Tomography, Circ Cardiovasc Imaging, 3, 1, pp. 41-46.
Mccommis et al. (2009)—Myocardial Blood Volume is Associated with Myocardial Oxygen Consumption: An Experimental Study with CMR in a Canine Model, JACC Cardiovasc Imaging, 2, 11, pp. 1313-1320.
Menendez et al. (2009)—Fatty acid synthase: Association with insulin resistance, type 2 diabetes, and cancer, Clinical Chemistry, 55, 3, pp. 425-438.
Mills et al. (2014)—The society for vascular surgery lower extremity threatened limb classification system: Risk stratification based on Wound, Ischemia, and foot Infection (WIfI), Journal of Vascular Surgery, 59, 1, pp. 220-234.
Miyashita et al. (2011)—Cilostazol increases skin perfusion pressure in severely ischemic limbs, Angiology, 62, 1, pp. 15-17.
Money et al. (1998)—Effect of cilostazol on walking distances in patients with intermittent claudication caused by peripheral vascular disease, Journal of Vascular Surgery, 27, 2, pp. 267-275.
Mostad et al. (2006)—Effects of n-3 fatty acids in subjects with type 2 diabetes: reduction of insulin sensitivity and time-dependent alteration from carbohydrate to fat oxidation 1-3, Am J Clin Nutr, 84, pp. 540-550.
Mueller et al. (2013)—Weight-bearing versus nonweight-bearing exercise for persons with diabetes and peripheral neuropathy: A randomized controlled trial, Archives of Physical Medicine and Rehabilitation, 94, 5, pp. 829-838.
Nahid et al. (2011)—Tuberculosis biomarker and surrogate endpoint research roadmap, American Journal of Respiratory and Critical Care Medicine, 184, 8, pp. 972-979.
Nakamura et al. (2003)—Effects of cilostazol on serum lipid concentrations and plasma fatty acid composition in type 2 diabetic patients with peripheral vascular disease, Clin Exp Med, 2, 4, pp. 180-184.
Naslund et al. (2015)—Feasibility of Popular m-Health Technologies for Activity Tracking Among Individuals with Serious Mental Illness, Telemedicine and e-Health, 21, 3, pp. 213-216.
Nather et al. (2008)—Epidemiology of diabetic foot problems and predictive factors for limb loss, Journal of Diabetes and its Complications, 22, 2, pp. 77-82.
Niki, Mori (1985)—Phase I Study of Cilostazol: Safety evaluation at increasing single doses in healthy volunteers, Arzneimittelforschung, 35, 7A, pp. 1173-1185.
Pantalone et al. (2018)—Effect of glycemic control on the Diabetes Complications Severity Index score and development of complications in people with newly diagnosed type 2 diabetes, Journal of Diabetes, 10, 3, pp. 192-199.
Park et al. (2006)—Decreased muscle strength and quality in older adults with type 2 diabetes: The health, aging, and body composition study, Diabetes, 55, 6, pp. 1813-1818.
Park et al. (2009)—Excessive loss of skeletal muscle mass in older adults with type 2 diabetes, Diabetes Care, 32, 11, pp. 1993-1997.
Pecoraro, Reiber, Burgess (1990)—Pathways to diabetic limb amputation: Basis for prevention, Diabetes Care, 13, 5, pp. 513-521.
Petersson et al. (2009)—Relationships between serum fatty acid composition and multiple markers of inflammation and endothelial function in an elderly population, Atherosclerosis, 203, 1, pp. 298-303.
Pratt (2001)—Analysis of the cilostazol safety database., The American journal of cardiology, 87, 12 A, pp. 28D-33D.
Ramsey et al. (1999)—Patient-level estimates of the cost of complications in diabetes in a managed-care population, PharmacoEconomics, 16, 3, pp. 285-295.
Razani et al. (2011)—Fatty acid synthase modulates homeostatic responses to myocardial stress, Journal of Biological Chemistry, 286, 35, pp. 30949-30961.
Resnick, Gordon (2014)—Effects of cilostazol on arterial wound healing: A retrospective analysis, Annals of Vascular Surgery, 28, 6, pp. 1513-1521.
Rioux, Legrand (2007)—Saturated fatty acids: Simple molecular structures with complex cellular functions, Current Opinion in Clinical Nutrition and Metabolic Care, 10, 6, pp. 752-758.
Rosales, Santos, Mercado-Asis (2011)—Cilostazol: a pilot study on safety and clinical efficacy in neuropathies of diabetes mellitus type 2 (ASCEND), Angiology, 62, 8, pp. 625-635.
Rosenzweig et al. (2002)—Use of a disease severity index for evaluation of healthcare costs and management of comorbidities of patients with diabetes mellitus., The American journal of managed care, 8, 11, pp. 950-958.
Sadamoto, Bonde-Petersen, Suzuki (1983)—Skeletal muscle tension, flow, pressure, and EMG during sustained isometric contractions in humans, European Journal of Applied Physiology and Occupational Physiology, 51, 3, pp. 395-408.
Selby, Zhang (1995)—Risk factors for lower extremity amputation in persons with diabetes., Diabetes care, 18, 4, pp. 509-516.
Shaw, Sicree, Zimmet (2010)—Global estimates of the prevalence of diabetes for 2010 and 2030, Diabetes Research and Clinical Practice, 87, 1, pp. 4-14.
Singh, Armstrong, Lipsky (2005)—Preventing foot ulcers, Journal of the American Medical Association, 293, 2, pp. 94-96.
Soontornniyomkij et al. (2016)—Effects of HIV and Methamphetamine on Brain and Behavior: Evidence from Human Studies and Animal Models, Journal of Neuroimmune Pharmacology, 11, 3, pp. 495-510.

(56) References Cited

OTHER PUBLICATIONS

Stegeman et al. (2015)—A large scale analysis of genetic variants within putative miRNA binding sites in prostate cancer, Cancer Discov., 5, 4, pp. 368-379.

Tang et al. (2014)—Cilostazol effectively attenuates deterioration of albuminuria in patients with type 2 diabetes: a randomized, placebo-controlled trial, Endocrine, 45, 2, pp. 293-301.

Tavazzi et al. (2008)—Effect of n-3 polyunsaturated fatty acids in patients with chronic heart failure (the GISSI-HF trial): a randomised, double-blind, placebo-controlled trial, The Lancet, 372, pp. 1223-1230.

Vessby et al. (2001)—Substituting dietary saturated for monounsaturated fat impairs insulin sensitivity in healthy men and women: The KANWU study, Diabetologia, 44, 3, pp. 312-319.

Wakil (1989)—Fatty Acid Synthase, A Proficient Multifunctional Enzyme, Biochemistry, 28, 11, pp. 4523-4530.

Wang et al. (2003)—Plasma fatty acid composition and incidence of diabetes in middle-aged adults: The Atherosclerosis Risk in Communities (ARIC) Study., The American journal of clinical nutrition, 78, 1, pp. 91-98.

Wang et al. (2001)—Fatty acid synthase (FAS) expression in human breast cancer cell culture supernatants and in breast cancer patients, Cancer Lett, 167, 1, pp. 99-104.

Wang et al. (2004)—The human fatty acid synthase gene and de novo lipogenesis are coordinately regulated in human adipose tissue., The Journal of nutrition, 134, 5, pp. 1032-1038.

Wang et al. (2002)—A New Model ELISA, Based on Two Monoclonal Antibodies, for Quantification of Fatty Acid Synthase, Journal of Immunoassay and Immunochemistry, 23, 3, pp. 279-292.

Wang et al. (2004)—Fatty acid synthase as a tumor marker: its extracellular expression in human breast cancer, Journal of Experimental Therapeutics and Oncology, 4, pp. 101-110.

Wei et al. (2016)—Fatty acid synthesis configures the plasma membrane for inflammation in diabetes, Nature, 539, 7628, pp. 294-298.

Wu et al. (2011)—Antidiabetic and antisteatotic effects of the selective fatty acid synthase (FAS) inhibitor platensimycin in mouse models of diabetes, Proceedings of the National Academy of Sciences, 108, 13, pp. 5378-5383.

Yokoyama et al. (2007)—Effects of eicosapentaenoic acid on major coronary events in hypercholesterolaemic patients (JELIS): a randomised open-label, blinded endpoint analysis, Lancet, 369, 9567, pp. 1090-1098.

Young et al. (2008)—Diabetes complications severity index and risk of mortality, hospitalization, and healthcare utilization., The American Journal of Managed Care, 14, 1, pp. 15-23.

Zhang et al. (2016)—Cilostazol can increase skin oxygen supply assessed by transcutaneous oxygen pressure measurement in type 2 diabetes with lower limb ischemic disease a randomized trial, Journal of Wound, Ostomy and Continence Nursing, 43, 3, pp. 254-259.

Zheng et al. (2014)—Noncontrast skeletal muscle oximetry, Magnetic Resonance in Medicine, 71, 1, pp. 318-325.

Zheng et al. (2014)—A pilot study of regional perfusion and oxygenation in calf muscles of individuals with diabetes with a noninvasive measure, Journal of Vascular Surgery, 59, 2, pp. 419-426.

Zheng et al. (2015)—Non-contrast MRI perfusion angiosome in diabetic feet, European Radiology, 25, 1, pp. 99-105.

Zock et al. (1997)—Fatty acids in serum cholesteryl esters as quantitative biomarkers of dietary intake in humans., American journal of epidemiology, 145, 12, pp. 1114-1122.

Zolli (2004)—Foot ulceration due to arterial insufficiency: role of cilostazol, Journal of Wound Care, 13, 2, pp. 45-47.

\* cited by examiner

PRIOR ART

PRIOR ART

METHODS OF DETECTION AND TREATMENT FOR CARDIOVASCULAR DISEASE AND FOOT WOUNDS

CROSS-REFERENCE TO RELATED APPLICATIONS

This application claims priority from U.S. Provisional Application Ser. No. 62/492,447 filed on 1 May 2017, which is incorporated herein by reference in its entirety.

STATEMENT REGARDING FEDERALLY SPONSORED RESEARCH OR DEVELOPMENT

This invention was made with government support under HL132060 awarded by the National Institutes of Health. The government has certain rights in the invention.

MATERIAL INCORPORATED-BY-REFERENCE

Not applicable.

FIELD OF THE INVENTION

The present disclosure generally relates to detection of a biomarker for cardiovascular disease and treatment of cardiovascular disease in a subject in need thereof and improved treatment methods for subjects with diabetes.

BACKGROUND OF THE INVENTION

Cerebrovascular events increase from 1.8 to 6-fold in patients with diabetes. 20% of diabetic patients have progression of carotid artery stenosis. Diabetic patients are 6× more likely to have a stroke (Gregg E, et al. N Engl J of Med, 2014;370(16)).

Foot wounds (FWs) are a major health issue in patients with Type 2 Diabetes (T2D) and can cause profound emotional, physical, and financial stress on patients and their families. It is one of the most prevalent and most expensive T2D-associated complications, and up to 70% of FWs will fail to heal. Although several adjunct therapies have been proposed for the treatment of FWs in patients with T2D, there are currently no oral pharmacological agents that are Food and Drug Administration (FDA)-approved, and no validated serum biomarkers to assess FW healing potential.

SUMMARY OF THE INVENTION

Among the various aspects of the present disclosure is the provision of a method of detection of cardiovascular disease or foot wound, and monitoring treatment response by detection of a novel biomarker. Also provided are methods of treatment of a cardiovascular disease or a foot wound.

An aspect of the present disclosure includes a method of detecting Fatty Acid Synthase (FAS). In some embodiments, the method can comprise providing a biological sample from a subject or detecting a level of FAS enzymatic activity or FAS content in the biological sample.

In some embodiments, the subject has diabetes or the biological sample is blood, plasma, or serum.

In some embodiments, the method comprises treating a subject for a foot wound or for a cardiovascular-related disease, disorder, or condition.

In some embodiments, the cardiovascular-related disease, disorder, or condition comprises a foot wound, carotid occlusive disease, arthrosclerotic disease, atherosclerosis, peripheral artery disease (PAD), or carotid artery stenosis.

In some embodiments, an elevated level of FAS in serum of subjects indicates the subject has T2D, increased probability of Diabetes Complications Severity Index (DCSI) or increased probability of having peripheral arterial disease (PAD) compared to a control.

In some embodiments, increased levels of FAS is indicate increased levels of serum LDL particles or increased levels of LDL particles deposited in high amounts in peripheral arterial plaque compared to a control.

Another aspect of the present disclosure includes a method of treating a foot wound or a cardiovascular-related disease, disorder, or condition in a subject in need thereof. In some embodiments, the method comprises: measuring a level of FAS in a biological sample obtained from a subject; or treating the subject having a foot wound or the cardiovascular-related disease, disorder, or condition with a therapeutic agent.

In some embodiments, the subject has a cardiovascular-related disease, disorder, or condition and is treated with a cardiac therapeutic agent if the level of FAS is greater than 3 or greater than the level of FAS measured in a control.

In some embodiments, the subject has diabetes or the biological sample is blood, plasma, or serum.

In some embodiments, a first FAS level is measured and a second FAS level is measured.

In some embodiments, (i) an elevated first FAS level compared to the second FAS level indicates foot wound healing; (ii) a elevated second FAS level compared to a first FAS level indicates foot wound progression; or (iii) an elevated second FAS level compared to a first FAS level indicates an increase in disease severity or disease progression.

In some embodiments, the subject has a foot wound, atherosclerotic disease, or PAD.

In some embodiments, the therapeutic agent is effective if the second FAS level is reduced compared to the first FAS level.

In some embodiments, the therapeutic agent is a vasodilator, optionally, cilostazol.

Another aspect of the present disclosure includes a method of diagnosing a cardiovascular-related disease, disorder, or condition. In some embodiments, the method comprises: providing a biological sample from a subject suspected of having a cardiovascular-related disease, disorder, or condition; detecting a FAS activity level in the biological sample; or comparing the FAS activity level of the subject and a control sample.

In some embodiments, the subject is diagnosed with a cardiovascular-related disease disorder, or condition if the FAS activity level in the subject is elevated compared to the FAS activity level in a control sample or the FAS activity level in the biological sample is greater than 3.

In some embodiments, the method comprises treating a subject for a cardiovascular-related disease, disorder, or condition.

In some embodiments, the cardiovascular-related disease, disorder, or condition comprises a foot wound, carotid occlusive disease, arthrosclerotic disease, atherosclerosis, peripheral artery disease (PAD), or carotid artery stenosis.

In some embodiments, the subject has diabetes or the biological sample is blood, plasma, or serum.

In some embodiments, the FAS is circulating plasma FAS or serum FAS.

In some embodiments, the control subject does not have a cardiovascular-related disease or an arterial occlusive disease.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

FIG. 9B. cFAS is elevated in subjects with T2D (n=40) compared to no T2D (n=41). FIG. 9C. cFAS is also elevated in subjects with DCSI ≥5 (n=15) compared to DCSI <5 (n=14).

FIG. 11A. In our current clinical practice, Cilostazol therapy is currently administered to only a minority of subjects, and therefore the majority of patients would likely meet study eligibility criteria. FIG. 11B. Subjects with T2D and PAD who receive Cilostazol therapy have lower cFAS (whiskers indicate max and min values) in study cohort.

FIG. 14A. Total blood and tissue specimens collected. Linked tissue is collected under a specific protocol that also allows collection of patient demographics. FIG. 14B. Blood and tissue specimens collected from patients with linked demographics.

DETAILED DESCRIPTION OF THE INVENTION

Figure 1:
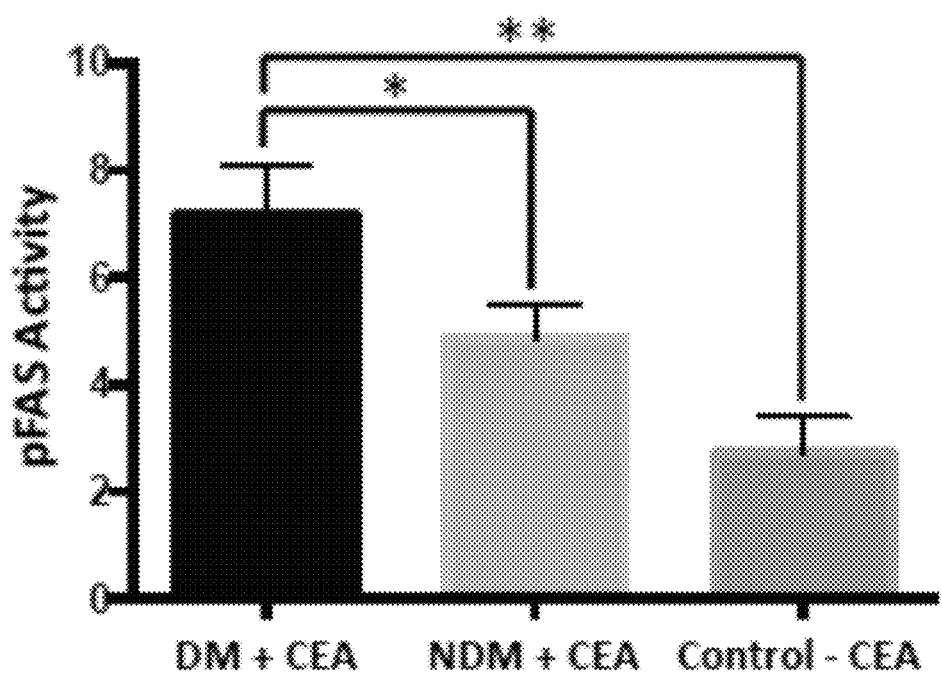
FIG. 1 is a bar graph of pFAS activity. pFAS is elevated in diabetic patients with high grade carotid occlusive disease.
Figure 2:
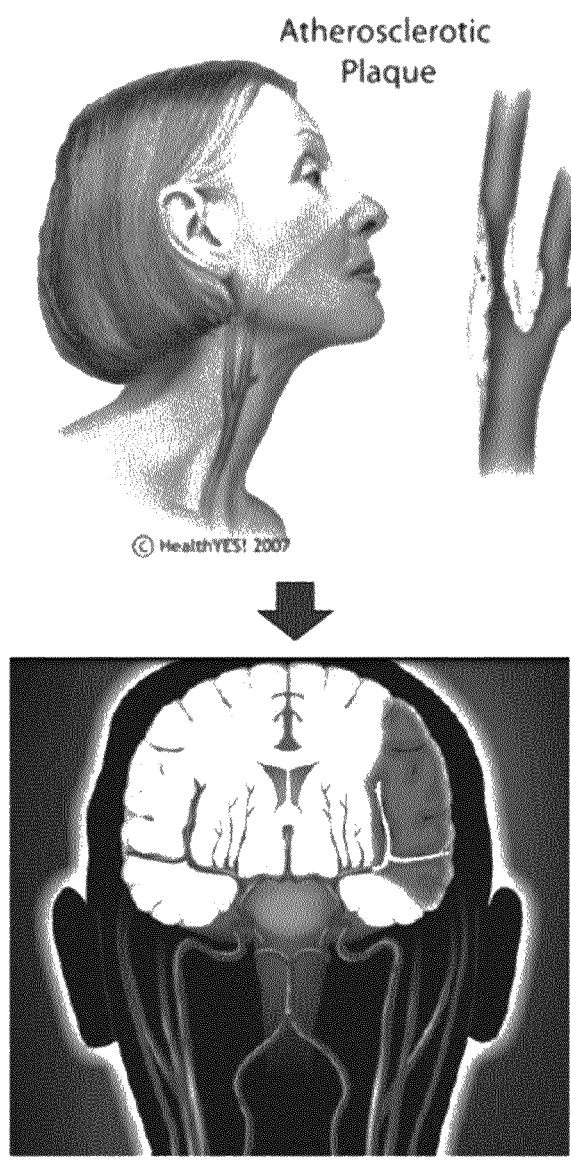
FIG. 2 is an illustration of an atherosclerotic plaque.
Figure 3:
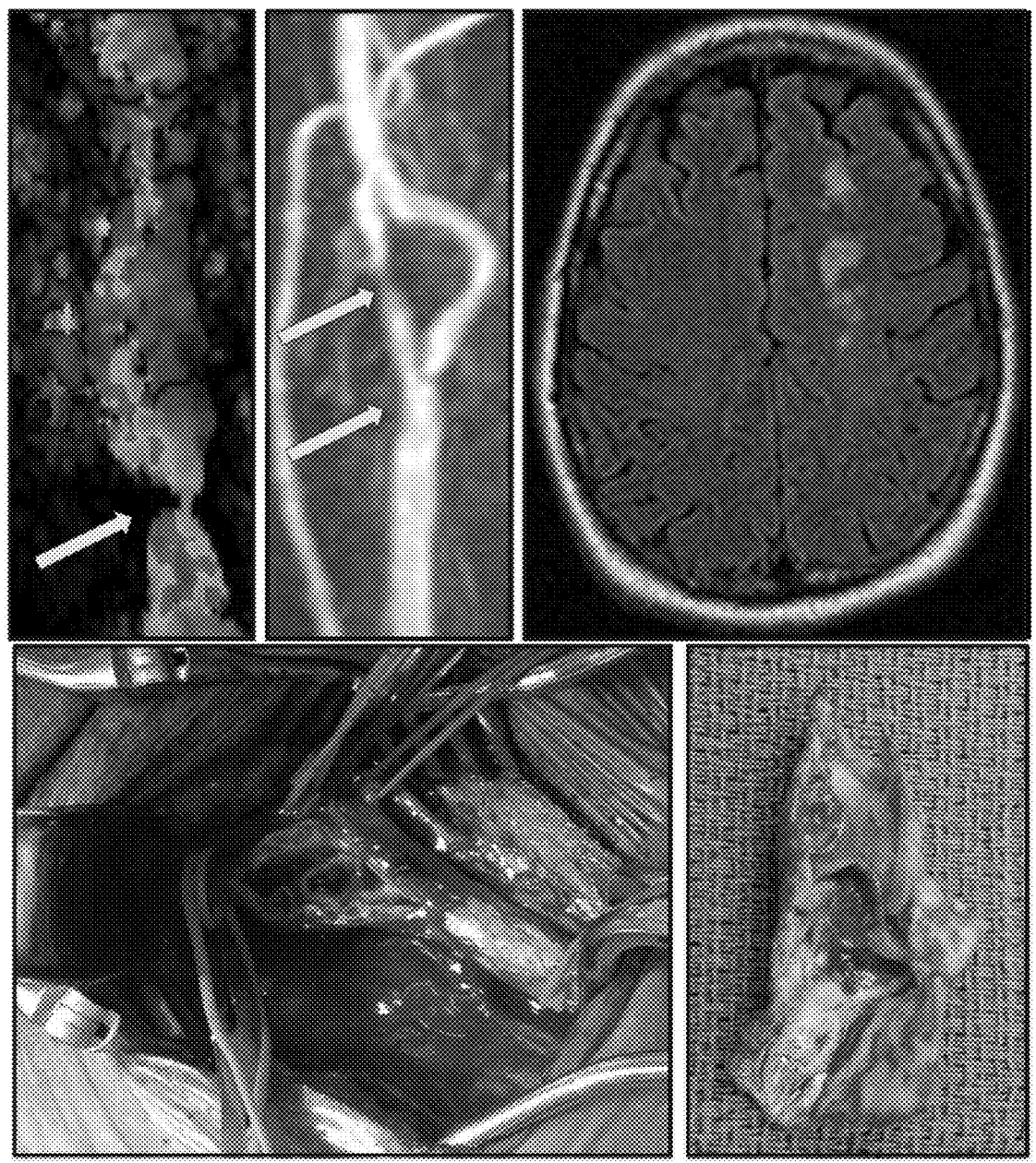
FIG. 3 is a series of images of an atherosclerotic plaque.
Figure 4A:
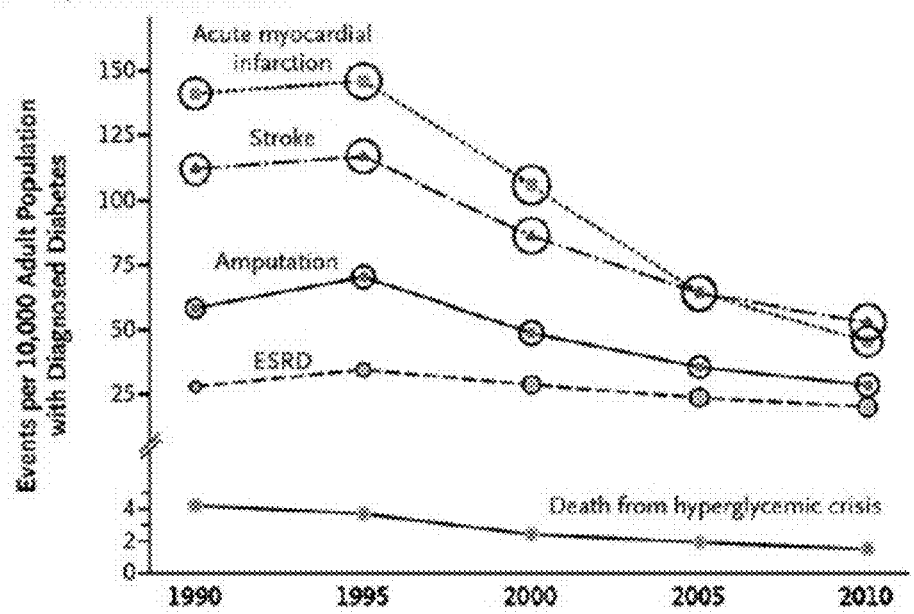
FIG. 4A-FIG. 4B is a series of bar graphs showing increased cardiac events in diabetes patients and overall adult population.
Figure 4B:
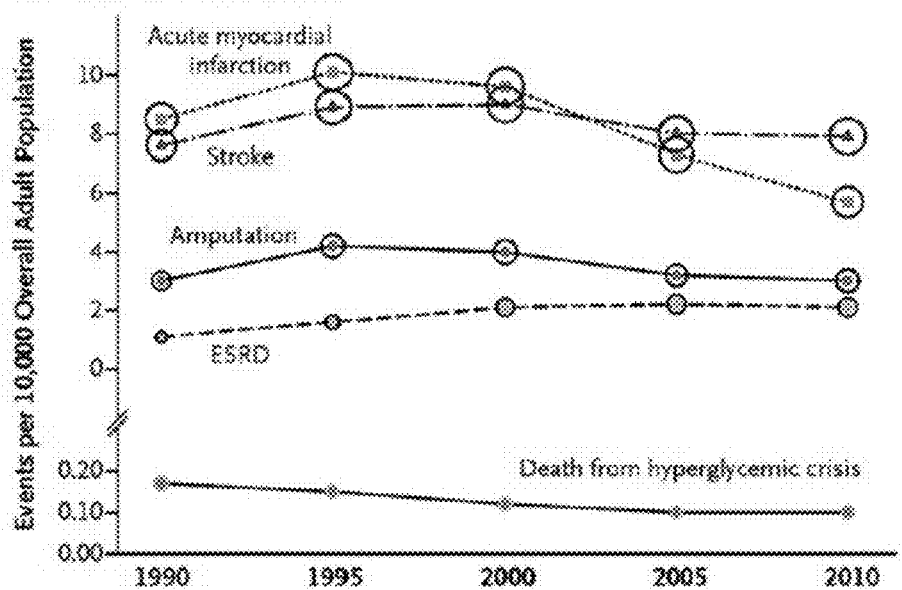
Figure 5:
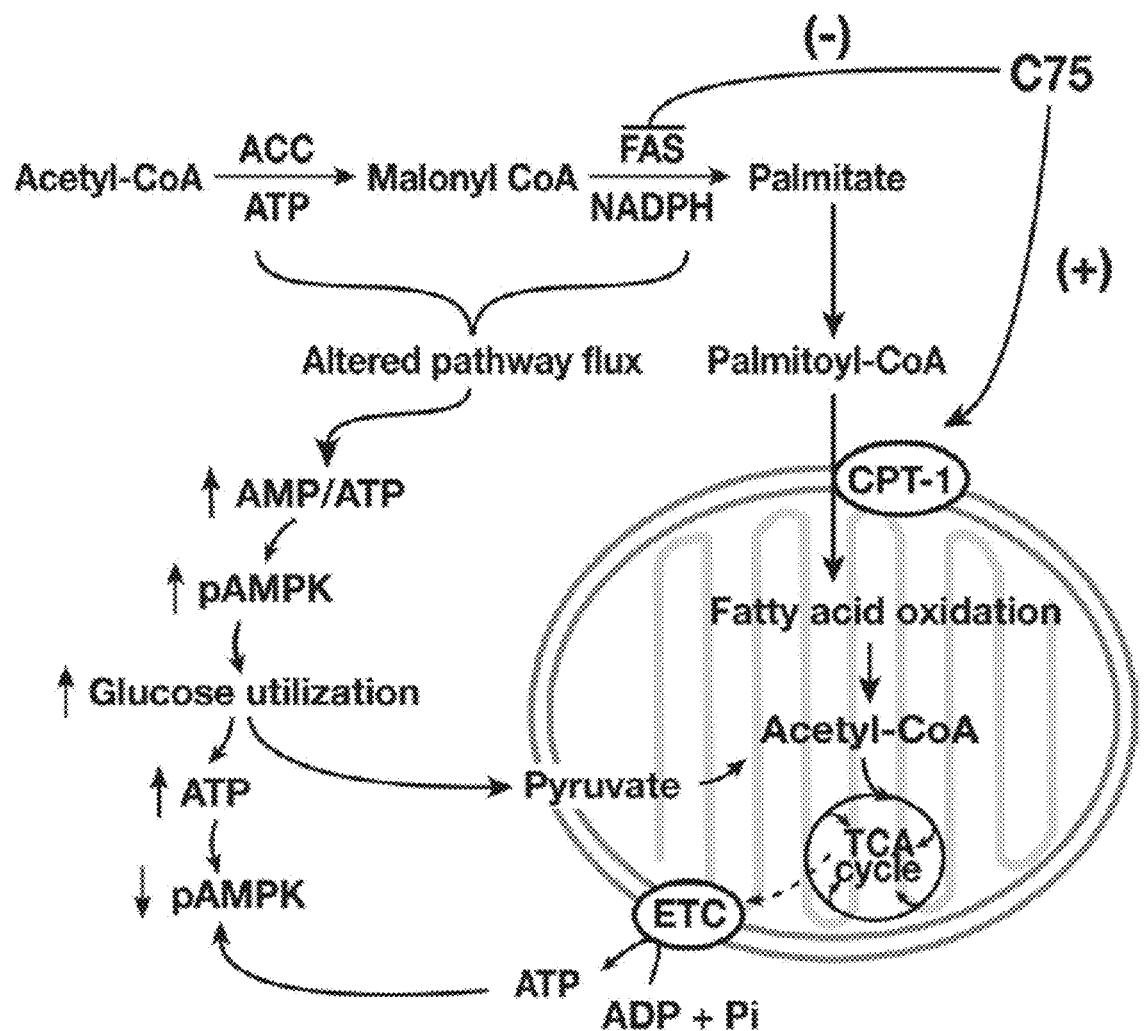
FIG. 5 is an illustration of the circulating FAS (pFAS).

The present disclosure is based, at least in part, on the discovery that plasma FAS is a biomarker of peripheral arterial disease in setting of diabetes. As shown herein, pFAS is present and is enzymatically active in the plasma and serum of patients with advanced atherosclerotic disease. Furthermore, as shown herein, diabetic patients appear to have higher pFAS activity levels; pFAS activity appears to correlate with fasting plasma triglycerides; and pFAS predominantly fractionates with LDL plasma fractions, which suggests possible association with this lipoprotein.

A major challenge in the management of patients with advanced cardiovascular disease is characterization of severity of disease and likelihood to respond to treatment. Our data suggests that pFAS correlates with severity of atherosclerotic disease in diabetic patients. Interestingly we also find that pFAS may correlate and associate with plasma lipoprotein profiles, which may affect lipoprotein role in atherogenesis and atheroprogression.

Fatty Acid Synthase (FAS)

The present disclosure provides for the detection of fatty acid synthase (FAS) for the detection and monitoring of disease, disease progression, or wound healing progression. For example, FAS can be circulating plasma FAS (pFAS) or serum circulating FAS (cFAS).

Diabetes is currently known to be a chronic metabolic disorder characterized by hyperglycemia. In addition, tissue fatty acid and phospholipid synthesis (phospholipogenesis) are significantly altered in diabetic patients leading to differential expression of lipid species in various tissue beds (e.g. heart, liver, adipose tissue). Central to this is the enzyme Fatty Acid Synthase (FAS), which is a multiunit enzyme that catalyzes synthesis of long-chain fatty acids from acetyl-CoA and malonyl-CoA.

Recently, it is observed that circulating plasma FAS (pFAS) can also affect tissue and biological responses in specific disease states, however its potential role in vascular atheroprogression and plaque stability is unknown.

The activity of pFAS in the fasting serum of 30 patients (15 diabetic; 15 non-diabetic) undergoing carotid endarterectomy (CEA), as well as 15 control patients with no evidence of arterial occlusive disease were compared. Diabetic patients were more likely to be hypertensive and receive metformin compared to non-diabetic patients (P<0.05). Patients with no evidence of arterial occlusive disease were <60 years old, and had no cardiovascular morbidities. Diabetic patients undergoing CEA demonstrated a 39% increase in pFAS activity compared to non-diabetic patients undergoing CEA (P=0.04), and a 91% increase compared to patients with no arterial occlusive disease (P<0.001). However, there was no significant difference in pFAS protein expression among diabetic and non-diabetic patients. pFAS did not correlate with fasting plasma glucose, but demonstrated a mild correlation with fasting plasma triglycerides ($R^2$=0.4, P=0.03). Fast protein liquid chromatography (FPLC) fractionation of plasma from diabetic and non-diabetic patients revealed that pFAS predominately fractionates with LDL plasma fractions.

These findings suggest pFAS activity is altered in diabetic patients with high-grade atherosclerotic disease, and that pFAS is associated with plasma lipoprotein profiles that can affect cardiovascular morbidity (see e.g., Example 1).

Example 2 describes the measurement of cFAS in subjects with diabetes with foot wounds and treated with Cilostazol. These studies show (1) cFAS is significantly elevated among subjects with more clinically severe PAD and T2D and (2) patients with T2D who were taking Cilostazol therapy, cFAS was significantly lower compared to subjects who were not receiving the medication.

Unlike conventional biomarkers, the FAS detection as described herein is detected by FAS enzymatic activity, not merely just the content or presence of a known biomarker. Furthermore, Fatty Acid Synthase (FAS), an essential multiunit enzyme that catalyzes the synthesis of long-chain fatty acids from acetyl-CoA and malonyl-CoA, was only recently found to circulate in the plasma (pFAS). As such, detection of FAS is unconventional.

Cardiovascular-Related Disease, Disorder, or Condition

As described herein, the present disclosure provides for a new biomarker of cardiovascular disease. For example, the present disclosure showed that FAS is associated with cardiovascular-related diseases, disorders, or conditions.

A cardiovascular-related disease can be any disease related to a disease, disorder, or condition of the heart and vasculature. For example, a cardiovascular-related disease can be aneurysm, angina, arrhythmia, atherosclerosis, atrial fibrillation, cardiomyopathy, cardiovascular disease (CVD), cardiovascular mortality, cerebral vascular disease, cerebrovascular heart disease, congenital heart disease, coronary heart disease (CHD), coronary artery disease, heart attack, heart disease, heart failure (HF), heart valve disease, heart valve problems, high blood pressure (hypertension), hypertensive heart disease, infective endocarditis, inflammatory heart disease, ischemic heart disease, rheumatic heart disease, stroke (e.g., ischemic stroke, hemorrhagic stroke), sudden death, transient ischemic attack, peripheral arterial disease, pericardial disease, or valvular heart disease.

In one embodiment, the cardiovascular-related disease can be atherosclerosis. Atherosclerosis (e.g., peripheral artery disease (PAD), diabetes-induced PAD, hypertension, arterial stenosis, carotid artery disease) is the hardening and narrowing of the arteries, which blocks the arteries putting blood flow at risk. Atherosclerosis is implicated as the cause of heart attacks, strokes, and peripheral vascular disease—what together are called cardiovascular disease.

Diabetes

As described herein, the present disclosure provides for a new biomarker of diabetes. For example, the present disclosure showed that FAS is associated with diabetes.

Type 2 Diabetes (T2D) is a generic clinical term that can be often applied to represent a wide spectrum of metabolic derangement in patients with hyperglycemia, insulin resistance, and relative lack of insulin production.

Foot Wounds

As described herein, the present disclosure provides for a new biomarker of evaluating healing in subjects with foot wounds. For example, the present disclosure showed that FAS is associated with impaired healing.

Foot wounds (FWs) are a major health issue in patients with Type 2 Diabetes (T2D) and can cause profound emotional, physical, and financial stress on patients and their families. It is one of the most prevalent and most expensive T2D-associated complications, and up to 70% of FWs will fail to heal. Although several adjunct therapies have been proposed for the treatment of FWs in patients with T2D, there are currently no oral pharmacological agents that are Food and Drug Administration (FDA)-approved, and no validated serum biomarkers to assess FW healing potential. A serum biomarker that can effectively predict, diagnose, and monitor FW healing in patients with T2D is needed. An effective oral pharmacological therapy that can improve FW healing is also needed, and would lead to an important paradigm shift in the management of patients with T2D. Furthermore, there is currently a lack of a national biorepository devoted for translational research on FWs in patients with T2D.

Foot wounds (FWs) occur in 15-20% of individuals with Type 2 Diabetes (T2D). Up to 70% of these FWs fail to heal, develop an infection, or progress to partial or complete limb loss with lower extremity amputation. In addition to the profound emotional and physical distress that patients endure from limb loss, FWs in aggregate are also associated with substantial direct and indirect financial costs that are estimated to exceed $250 billion per year. Despite the importance of this public health problem, there is a paucity of validated serum biomarkers to assess healing potential and identify patients who are at higher risk of failure to heal. Although there are a few Food and Drug Administration (FDA)-approved treatments for FW in patients with T2D, there are currently no FDA-approved oral pharmacological therapies to help improve FW healing in this population.

Therapeutic Agent

As described herein, a subject suspected of having or a subject diagnosed with a foot wound or a cardiovascular-related disease, disorder, or condition can be treated by any method known in the art suitable for treating the disease, disorder, or condition. Therapeutic agents and methods of treating a foot wound or cardiovascular-related disease, disorder, or condition are well known in the art.

For example, a therapeutic agent can be any therapeutic agent suitable for treating a foot wound or a cardiovascular-related disease, disorder, or condition or any agent suitable to avoid cardiovascular mortality or non-cardiovascular mortality.

As another example, a therapeutic agent can be a phosphodiesterase inhibitor (e.g., cilostazol, a vasodilator), an ACE inhibitor (e.g., a vasodilator, which opens blood vessels more fully and can help reduce high blood and slow heart failure), an anti-arrhythmic medication (helps restore a normal pumping rhythm to the heart), antibiotics (help to prevent the onset of infections), anticoagulants ("blood thinners" to reduce the risk of developing blood clots from poorly circulating blood around faulty heart valves), beta-blockers (can reduce the heart's workload by helping the heart beat slower, reduce palpitations), calcium channel blockers, diuretics ("water pills" to reduces amount of fluid in the tissues and bloodstream which can lessen the workload on the heart), vasodilators (can lower the heart's work by opening and relaxing the blood vessels; reduced pressure may encourage blood to flow in a forward direction, rather than being forced backward through a leaky valve), a thrombolytic agent, an anticonvulsant agent, an anti-platelet agent, an anti-coagulant agent or a hematologic agent, an analgesic, a beta blocker or alpha activity agent, an ACE inhibitor, a calcium channel blocker, a vasodilator, a cholesterol-lowering and blood-pressure-lowering medicine, a blood pressure medicine, or medicines used to treat depression and pain.

As another example, a therapeutic agent can be an anticoagulant such as Warfarin (for example, Coumadin, Jantoven), Heparin, Dabigatran (Pradaxa), Rivaroxaban (Xarelto), Apixaban (Eliquis), or Edoxaban (Savaysa). As another example, a therapeutic agent can be a thrombolytic such as an IV tissue plasminogen activator (TPA) or Alteplase (Activase). As another example, a therapeutic agent can be an antiplatelet medication such as aspirin (for example, Bayer) or aspirin combined with dipyridamole (Aggrenox), Clopidogrel (Plavix), Prasugrel (Effient), or Ticagrelor (Brilinta). As another example, a therapeutic agent can be a cholesterol-lowering and blood-pressure-lowering medicines such as a statin (e.g., Atorvastatin (Lipitor), Rosuvastatin (Crestor)), angiotensin II receptor blockers (ARBs), angiotensin-converting enzyme (ACE) inhibitors, beta-blockers, calcium channel blockers, diuretics, Nicotinic Acids (e.g., Lovastatin (Advicor)), Cholesterol Absorption Inhibitors (e.g., Ezetimibe/Simvastatin (Vytorin)). As another example, a therapeutic agent can be a diuretic such as Amiloride (Midamor), Bumetanide (Bumex), Chlorothiazide (Diuril), Chlorthalidone (Hygroton), Furosemide (Lasix), Hydro-chlorothiazide (Esidrix, Hydrodiuril), Indapamide (Lozol, or Spironolactone (Aldactone). As another example, a therapeutic agent can be a medicine used to treat depression and pain such as amitriptyline, bupropion (Wellbutrin), citalopram (Celexa), fluoxetine (Prozac), sertraline (Zoloft), venlafaxine (Effexor). As another example, a therapeutic agent can be an anticonvulsant such as Diazepam (Valium) or Lorazepam (Ativan). As another example, a therapeutic agent can be an analgesic such as acetaminophen (Tylenol, Feverall, Aspirin Free Anacin). As another example, a therapeutic agent can be a beta blocker or alpha activity medication such as Labetalol (Normodyne, Trandate), Acebutolol (Sectral), Atenolol (Tenormin), Betaxolol (Kerlone), Bisoprolol/hydrochlorothiazide (Ziac), Bisoprolol (Zebeta), Metoprolol (Lopressor, Toprol XL), Nadolol (Corgard), Propranolol (Inderal), or Sotalol (Betapace). As another example, a therapeutic agent can be a digitalis preparation (e.g., Digoxin, Digitoxin) such as Lanoxin. As another example, a therapeutic agent can be a combined alpha and beta blocker such as carvedilol or labetalol hydrochloride. As another example, a therapeutic agent can be an ACE Inhibitor such as Enalapril (Vasotec), Benazepril (Lotensin), Captopril (Capoten), Enalapril (Vasotec), Fosinopril (Monopril), Lisinopril (Prinivil, Zestril), Moexipril (Univasc), Perindopril (Aceon), Quinapril (Accupril), Ramipril (Altace), or Trandolapril (Mavik). As another example, a therapeutic agent can be a calcium channel blocker such as Nicardipine (Cardene), Amlodipine (Norvasc, Lotrel), Diltiazem (Cardizem, Tiazac), Felodipine (Plendil), Nifedipine (Adalat, Procardia), Nimodipine (Nimotop), Nisoldipine (Sular), or Verapamil (Calan, Verelan). As another example, a therapeutic agent can be a vasodilator such as Nitroprusside sodium (Nipride, Nitropress, Sodium Nitroprusside), Isosorbide dinitrate (Isordil), Nesiritide (Natrecor), Hydralazine (Apresoline), Nitrates, or Minoxidil. As another example, a therapeutic agent can be an Angiotensin-2 Receptor Blockers (ARBs) or Angiotensin-2 Receptor Antagonists such as Candesartan (Atacand), Eprosartan (Teveten), Irbesartan (Avapro), Losartan (Cozaar), Telmisartan (Micardis), or Valsartan (Diovan). As another example, a therapeutic agent can be an Angiotensin-Receptor Neprilysin Inhibitor (ARNI) (a new drug combination of a neprilysin inhibitor and an ARB such as Sacubitril/valsartan (Entresto).

As another example, a therapeutic agent can be an agent that modulates FAS levels.

Formulation

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Md., 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutical active substances is well known in the art (see generally Remington's Pharmaceutical Sciences (A. R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, parenteral, pulmonary, oral, topical, intradermal, intramuscular, intraperitoneal, intravenous, subcutaneous, intranasal, epidural, ophthalmic, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

Therapeutic Methods

Also provided is a process of treating a foot wound or cardiovascular-related disease, disorder, or condition in a subject in need administration of a therapeutically effective amount of a therapeutic agent, so as to substantially inhibit a cardiovascular-related disease, disorder, or condition, slow the progress of a foot wound or cardiovascular-related disease, disorder, or condition, or limit the development of a foot wound or cardiovascular-related disease, disorder, or condition.

Methods described herein are generally performed on a subject in need thereof. A subject in need of the therapeutic methods described herein can be a subject having, diagnosed with, suspected of having, or at risk for developing a foot wound or cardiovascular-related disease, disorder, or condition. A determination of the need for treatment will typically be assessed by a history and physical exam consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, hamsters, guinea pigs, and chickens, and humans. For example, the subject can be a human subject.

Generally, a safe and effective amount of a therapeutic agent is, for example, that amount that would cause the desired therapeutic effect in a subject while minimizing undesired side effects. In various embodiments, an effective amount of a therapeutic agent described herein can treat a foot wound, substantially inhibit a cardiovascular-related disease, disorder, or condition, slow the progress of a cardiovascular-related disease, disorder, or condition, or limit the development of a cardiovascular-related disease, disorder, or condition.

According to the methods described herein, administration can be parenteral, pulmonary, oral, topical, intradermal, intramuscular, intraperitoneal, intravenous, subcutaneous, intranasal, epidural, ophthalmic, buccal, or rectal administration.

When used in the treatments described herein, a therapeutically effective amount of a therapeutic agent can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to treat a foot wound, substantially inhibit a cardiovascular-related disease, disorder, or condition, slow the progress of a foot wound or cardiovascular-related disease, disorder, or condition, or limit the development of a foot wound or a cardiovascular-related disease, disorder, or condition.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, $4^{th}$ ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Administration of a therapeutic agent can occur as a single event or over a time course of treatment. For example, a therapeutic agent can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to, concurrent with, or after conventional treatment modalities for a cardiovascular-related disease, disorder, or condition.

A therapeutic agent can be administered simultaneously or sequentially with another agent, such as an antibiotic, an anti-inflammatory, or another agent. For example, a therapeutic agent can be administered simultaneously with another agent, such as an antibiotic or an anti-inflammatory. Simultaneous administration can occur through administration of separate compositions, each containing one or more of a therapeutic agent, an antibiotic, an anti-inflammatory, or another agent. Simultaneous administration can occur through administration of one composition containing two or more of a therapeutic agent, an antibiotic, an anti-inflammatory, or another agent. A therapeutic agent can be administered sequentially with an antibiotic, an anti-inflammatory, or another agent. For example, a therapeutic agent can be administered before or after administration of an antibiotic, an anti-inflammatory, or another agent.

Administration

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration can be parenteral, pulmonary, oral, topical, intradermal, intramuscular, intraperitoneal, intravenous, subcutaneous, intranasal, epidural, ophthalmic, buccal, or rectal administration.

Agents and compositions described herein can be administered in a variety of methods well known in the arts. Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 μm), nanospheres (e.g., less than 1 μm), microspheres (e.g., 1-100 μm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump which may be used to administer the agent or composition in a manner similar to that used for delivering insulin or chemotherapy to specific organs or tumors. Typically, using such a system, an agent or composition can be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; or improve shelf life of the product.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: Diabetes Influences Circulating FAS in Patients with Carotid Artery Stenosis The following example shows that pFAS is a biomarker of carotid arterial occlusive disease in the setting of diabetes. It was found that pFAS is elevated in diabetic patients with high grade carotid occlusive disease and pFAS correlates with plasma TGs, but not plasma glucose.

Plasma lipid abnormalities associated with diabetes are thought to contribute to atherogenesis and overall cardiovascular morbidity. Fatty Acid Synthase (FAS), an essential multiunit enzyme that catalyzes the synthesis of long-chain fatty acids from acetyl-CoA and malonyl-CoA, was recently found to circulate in the plasma (pFAS). Since FAS is essential for the lipogenic functions of the liver and adipose tissue, and its tissue expression is altered in the setting of diabetes, we sought to evaluate whether pFAS is a biomarker for arterial occlusive disease in diabetic patients. To test this hypothesis, we compared the activity of pFAS in the fasting serum in a relatively homogenous group of 15 diabetic (DM) and 15 non-diabetic (NDM) patients who are undergoing carotid endarterectomy (CEA). We also evaluated pFAS in 15 additional control patients who have no evidence of arterial occlusive disease. Among selected patients, DM patients were more likely to have hypertension and receive metformin compared to NDM patients (P<0.05). Control patients who have no evidence of arterial occlusive disease were all <60 years old, and none had cardiovascular morbidities. DM patients undergoing CEA demonstrated a 39% increase in pFAS activity compared to NDM patients undergoing CEA (P=0.04), and a 91% increase compared to control patients (P<0.001). Similarly, on Western blot analysis DM patients demonstrated a 3.7% increase in pFAS expression compared to NDM patients, and 27% increase compared to control patients. pFAS did not correlate with fasting plasma glucose, LDL, HDL, or total cholesterol, but demonstrated a modest correlation with fasting plasma triglycerides ($R^2=0.4$, P=0.03). These findings suggest pFAS activity is altered in DM patients with carotid artery stenosis, and correlates with specific plasma lipid profiles suggestive of overall cardiovascular morbidity.

Figure 6:
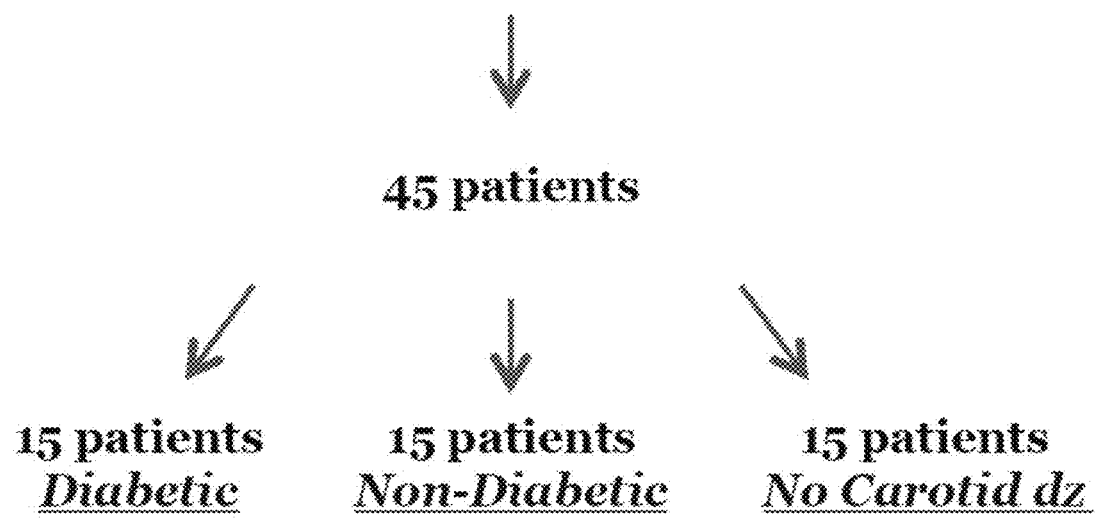
FIG. 6 shows the patient selection and population.
Figure 7:
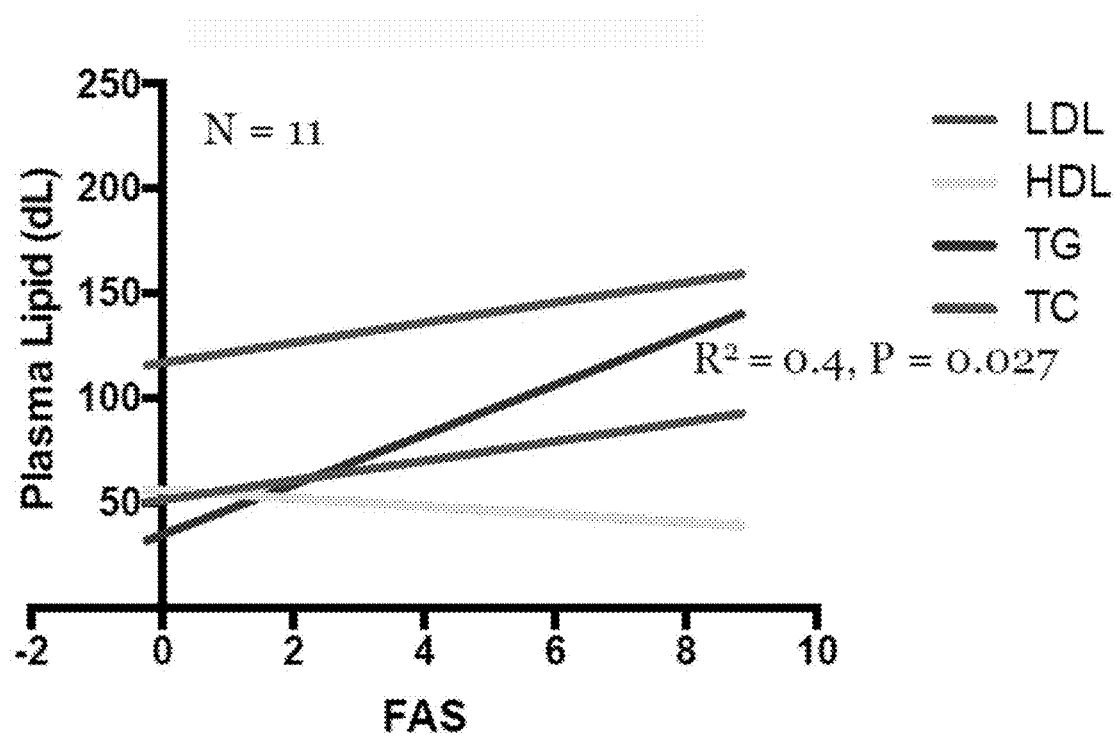
FIG. 7 is a graph showing correlation of FAS levels for various plasma lipids, including low-density lipoprotein (LDL), high-density lipoprotein (HDL), triglyceride (TG), and total cholesterol (TC). pFAS correlates with plasma TGs.
Figure 8:
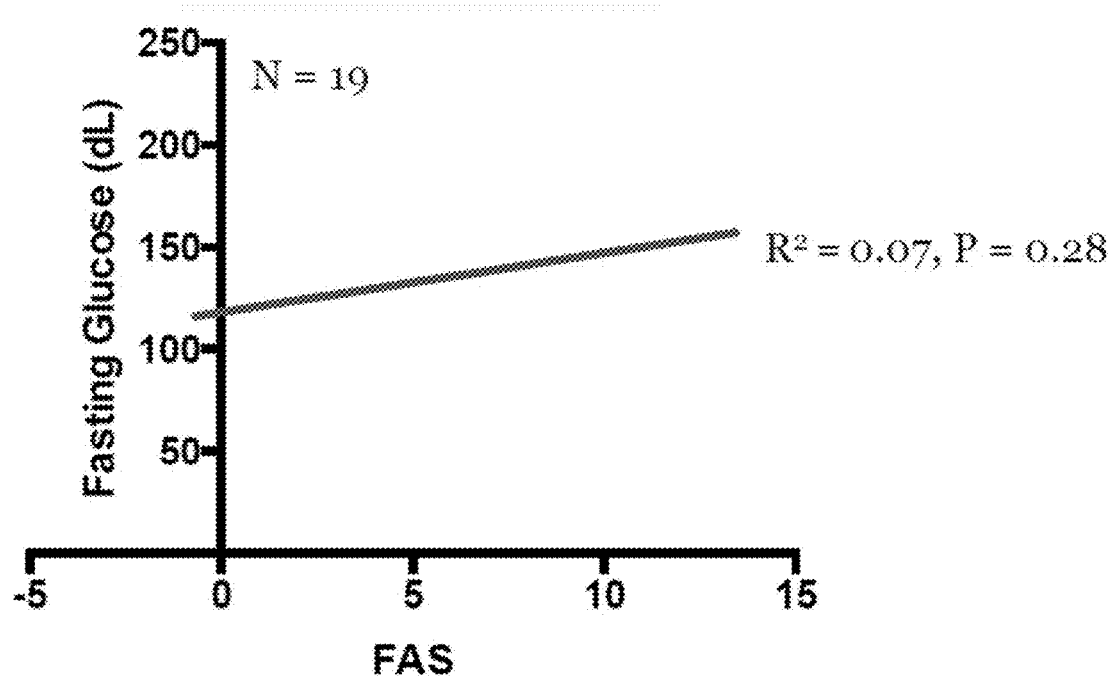
FIG. 8 is a graph showing correlation of FAS to glucose levels. pFAS does not correlate with plasma glucose.

FIG. 6 shows the patient selection. FIG. 1 is a bar graph of pFAS activity showing pFAS is elevated in diabetic patients with high grade carotid occlusive disease. FIG. 7 is a graph showing correlation of FAS levels for various plasma lipids showing pFAS correlates with plasma TGs. FIG. 8 is a graph showing correlation of FAS to glucose levels showing pFAS does not correlated with plasma glucose.

TABLE 1

|  | DM + CEA (n = 15) | NDM + CEA (n = 15) | NDM − CEA (n = 15) |
|---|---|---|---|
| DM | 100 | 0 | 0 |
| Gender (F) | 33 | 20 | 67 |
| Age |  |  |  |
| <50 | 0 | 0 | 80 |
| 50-60 | 13 | 13 | 13 |
| 61-70 | 33 | 33 | 0 |

TABLE 1-continued

|  |  | DM + CEA (n = 15) | NDM + CEA (n = 15) | NDM − CEA (n = 15) |
|---|---|---|---|---|
|  | 71-80 | 40 | 47 | 0 |
|  | >80 | 13 | 0 | 0 |
| BMI |  | 30 | 27 | 27 |
| Current Smoker |  | 0 | 0 | 7 |
|  | Symptomatic Carotid | 47 | 33 | 0 |
|  | Asymptomatic Carotid | 53 | 60 | 0 |
| Stroke |  | 27 | 27 | 0 |
| CAD |  | 20 | 33 | 0 |
| HTN |  | 93 | 53 | 0 |
| HLP |  | 87 | 93 | 0 |
| Arrhythmia |  | 27 | 7 | 0 |
| Valvular Heart Dz |  | 33 | 13 | 0 |
| Medications |  |  |  |  |
|  | ACE Inhibitor | 60 | 40 | 0 |
|  | Beta blocker | 60 | 40 | 0 |
|  | Aspirin | 73 | 73 | 7 |
|  | Other Antiplatelet | 33 | 40 | 0 |
|  | Statin | 100 | 93 | 0 |
|  | Insulin | 0 | 0 | 0 |
|  | Metformin | 60 | 0 | 0 |

Example 2: Fatty Acid Synthase, Cilostazol, and Diabetic Foot Wound Healing (FASCD Study)

In this example, we strive to improve the care of patients with Type 2 Diabetes and open foot wounds. We will study serum circulating Fatty Acid Synthase as a diagnostic and indicative biomarker for foot wounds relative diabetes clinical severity and treatment with Cilostazol. We will also develop an integrated biorepository for future translational research.

Subjects with T2D-associated complications (higher Diabetes Complications Severity Index; DCSI) have altered serum lipid profiles and fatty acid (FA) metabolism. Our group recently demonstrated that circulating Fatty Acid Synthase (cFAS), an essential enzyme responsible for de novo FA synthesis, is elevated in serum of subjects with T2D, and correlates with DCSI and the incidence of peripheral arterial disease (PAD) (see below). cFAS is also associated with serum LDL particles, and is deposited in high amounts in peripheral arterial plaque. Our central hypothesis is that serum cFAS is an important metabolic biomarker of disease severity in patients with T2D and open FWs, and that it can help predict the response to novel therapies.

Sources of Materials.

Demographic information and medical history will be obtained for all study participants. FW assessments will be performed, and serum will be collected, from participants in sections 1-3. Participants in section 3 will additionally receive foot functional assessments with ankle flexion angular velocity (AFAV) and 2-minute walk test, and perfusion assessments with transcutaneous oxygen pressure (TcPO2) and magnetic resonance (MR). MR perfusion assessment will also be performed.

(1) To Investigate the Effect of T2D Severity on Serum Circulating Fatty Acid Synthase (cFAS) Biomarker and FW Healing.

Here, we will investigate the effect of DCSI score on serum cFAS biomarker and FW healing. Despite optimal diabetes care, patients with high DCSI scores have a higher mortality and more frequent hospital admissions. Similarly, despite optimal wound care and off-loading maneuvers, patients with severely ischemic and/or infected FWs (as determined by WIfI wound classification) are less likely to heal and are more likely to result in an amputation. Prior studies evaluating serum biomarkers were hampered by inadequate normalization for T2D severity and FW class. Therefore, we propose a multi-center, prospective, cohort study, which adheres to FDA recommendations for wound healing clinical trials, and implements defined FW WIfI class inclusion criteria. We hypothesize that cFAS will be predictive of DCSI and FW healing, and that serum FA lipidomic assessments will help define the cFAS mechanism of action in patients with T2D.

Significance: Prevalence of T2D and Foot Wounds (FWs).

Over the last decade T2D has become a national and international health epidemic(1, 2). The Centers for Disease Control and Prevention reports that ~9% of the US population has T2D(3), and based on current trends it is estimated that 1 in 3 individuals may develop T2D by 2050(4). Approximately 25% of individuals with T2D will develop a FW at some point during the course of their chronic disease (5). These often present with slow and impaired healing, and are associated with high costs of diagnosis and treatment—exceeding $250 billion per year(6, 7). Despite the high level of care required for management of FWs, it is reported that up to 70% of individuals with T2D will still develop FW complications that ultimately lead to amputations(8, 9). Unlike reduced myocardial infarction and stroke rates in individuals with T2D(10), amputation rates have remained stubbornly high and essentially unchanged over the past decade(11). Patients with T2D are nearly 10 times more likely to receive a lower extremity amputation compared to patients who are non-diabetic(11). A feasible and translatable diagnostic strategy that identifies patients with T2D who are at higher risk of poor FW healing would be immensely beneficial in reducing the high morbidity associated with condition.

There are currently no reliable serum biomarkers to evaluate healing in individuals with T2D and open FWs. Healing of FWs in individuals with T2D is a complex multifactorial process that occurs when appropriate off-loading, debridement, and wound dressing are applied consistently(12, 13). However, despite standard of care, specific patient groups have impaired healing and are more prone to subsequent complications(14). Predictive, diagnostic, and indicative biomarkers previously proposed to identify such patient groups have been hampered by three main issues (15); 1) T2D is a generic clinical term that is often applied to represent a wide spectrum of metabolic derangement in patients with hyperglycemia, insulin resistance, and relative lack of insulin production; 2) FW study designs and outcome measures have not adequately reflected the etiological heterogeneity of FWs (e.g. ischemic, neurogenic, or mixed(13)) leading to mixed results when outcome measures do not take into consideration the severity of the FW(16); and 3) difficulty in biomarker monitoring over time leads to limited clinical feasibility and translation(17). As such, here is described a set of longitudinal clinical trials that adhere to FDA clinical trial recommendations on wound healing, as a strategy to evaluate a novel serum biomarker according to T2D complication severity and FW type.

Established Clinical Relevance of Diabetes Complication Severity Index (DCSI).

The DCSI is a validated 13-point scale scored from automated diagnostic, pharmacy, and laboratory data that are part of the typical standard of care(18). Unlike other risk engines(19, 20), and simple T2D complications counts, the DCSI was designed with the intention of allowing researchers and health plan administrators a reliable method to risk-adjust for severity of T2D(21). Recent studies show that patients with DCSI ≥5 have higher mortality and hospital admissions(18), and DCSI ≥11 are at highest risk for limb amputation(22). To our knowledge, our study is the first to utilize DCSI scores for risk-adjusted FW healing assessments and biomarker validation.

Novel Clinical Relevance of Circulating Serum Fatty Acid Synthase (cFAS).

Serum fatty acids (FAs) regulate insulin secretion(23) and sensitivity(24, 25), lipoprotein metabolism(24, 26), inflammatory markers(27), and endothelial function(26). Several multi-center human studies, such as the ARIC(28), SLIM (29), and KANWU(30), demonstrate that increased proportion of saturated fatty acids (SFAs) to poly-unsaturated fatty acids (PUFAs) is positively associated with the development of T2D and its associated complications. In addition to dietary intakes(26, 31, 32), de novo SFA lipogenesis is catalyzed by Fatty Acid Synthase (FAS)(33, 34), which is linked to visceral fat accumulation(35), obesity(36), and insulin resistance(37). Serum circulating FAS (cFAS) exists in the blood stream of individuals with cancer(38), and is a biomarker for malignant tumor virulence(39) as well as the clinical stage of neoplastic disease(40). We recently discovered that cFAS is elevated in patients with T2D, particularly those with high DCSI scores (≥5), and severe peripheral arterial disease (PAD; see data section below). These highly compelling findings suggest that cFAS is a clinically relevant biomarker of T2D disease severity. These studies will be the first to validate the clinical relevance of cFAS as a biomarker for FW healing in patients with T2D.

Innovation: High Throughput Serum cFAS Biomarker Profiling for Subjects with T2D and Open FWs.

These studies determine whether the enzymatically active serum cFAS is: 1) a diagnostic biomarker (can be used to identify FA profiles associated with T2D severity and FW healing); and 2) an indicative biomarker (can be used to monitor FW disease progression). cFAS content and enzyme activity will be evaluated using a high throughput 96-well assay platform. This makes our proposed study ideally suited for a multi-center trial format that will recruit a high number of patients.

Mobile Health Technology for Tracking Wound Healing.

Studies have shown that mobile tracking of wounds can be beneficial in directing therapy(44). We will implement such mobile health technology to accurately monitor FW healing on a weekly basis. This short-term monitoring will help with the detection of subtle changes in FW healing, and provide granular data to support our primary and secondary study endpoints (see below).

Data.

Figures 9A, 9B, 9C:
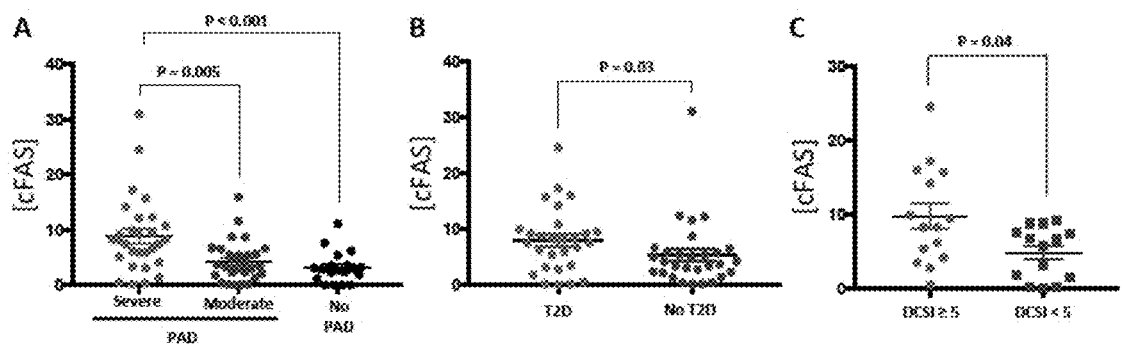
FIG. 9A-FIG. 9C is a series of graphs showing serum cFAS is a biomarker for disease subjects with PAD and T2D. cFAS was evaluated using 96-well ELISA (Aviva Systems Biology) FIG. 9A. Subjects with severe PAD (n=29) had more serum cFAS than subjects with moderate PAD (n=30), and subjects with no PAD (n=22).

Over a 1 year period, we collected serum specimens from subjects with peripheral arterial disease (PAD; severe or moderate), and/or T2D. Serum cFAS content and enzymatic activity was evaluated as a potential biomarker for PAD and T2D disease severity. FIG. 9 demonstrates that cFAS is significantly elevated among subjects with more clinically severe PAD and T2D (DCSI ≥5).

Subjects.

500 participants (100 subjects from Washington University) will be recruited, in a multi-center prospective cohort study. Inclusion criteria: 1) Age 18 or above; 2) T2D with DCSI (1-10); 3) have a chronic non-healing FW (lasting >1 month); 4) Society for Vascular Surgery (SVS) Wound (W), Ischemia (I), and foot Infection (fi; WIfI(45)) score of W≥1, I≤2, and fI≤2 (FIG. 10); 5) Rutherford Class 1 (mild claudication)-2 (moderate claudication); and 6) Are able and willing to receive FW evaluations and treatments per standard of care (e.g. off-loading, debridement, regular dressing changes)(46). Exclusion criteria: 1) DCSI ≥11; 2) taking oral dietary fish oil supplements (which are rich in FAs); 3) taking Cilostazol therapy; 4) have an active cancer or malignancy (which can increase cFAS); 5) anticipated amputation in the ipsilateral limb within 4 weeks of study enrollment; 6) and severe foot wound infection (i.e. purulence, cellulitis, extensive necrosis(47); WIfI score with fI of 3)(45).

Rationale for DCSI Inclusion Criteria.

Patients with DCSI ≥5 have an adjusted Hazard Ratio of 4.96 for hospitalization, and 5.1 for mortality within 5 years(18). We therefore propose to stratify our study subjects in to a low DCSI group (<5; Group 1) and a high DCSI group (≥5; Group 2). 50 subjects will be recruited into each group. Patients with DCSI ≥11 will be excluded given high amputation risk(22).

Rationale for Wound Type Inclusion Criteria.

The majority of FWs that occur in individuals with T2D are ischemic and/or neuroischemic in etiology (65%)(13). Subjects with these types of FWs are at significantly higher risk of limb loss than subjects with just purely neurogenic type wounds(48, 49). Implementation of the SVS WIfI scoring system(45) as part of our study inclusion criteria will help: 1) improve the feasibility of the study by including subjects that are regularly evaluated in our outpatient clinics and ER (see Recruitment and Feasibility Data section); 2) identify subjects who have a lower risk of amputation during the course of the study; 3) exclude subjects who have critical limb ischemia (CLI) who will likely require surgical arterial revascularization and/or partial and/or full foot amputation (9, 49, 50); 4) exclude subjects that have extensive infection that has high risk of failing standard medical therapy with antibiotic administration(45, 47). We anticipate these criteria will reduce potential confounding variables associated with FW etiology and severity.

Assessments.

Will occur at three time points: (1) at study enrollment, (2) 2-weeks following study enrollment (run-in phase), and (3) 4 months following study enrollment.

TABLE 2

Assessment time points.

| | Time Point (1): Baseline | Time Point (2): 2-weeks (run-in phase) | Time Point (3): 4-months following enrollment | Self-Assessments (App): weekly after enrollment |
|---|---|---|---|---|
| FWSA | X | X | X | X |
| WIfI Score | X | X | X | X |
| cFAS Content & Activity | X | | X | |
| Serum FA Content | X | | X | |

In-person FW assessments for Group 1 & 2 will occur at study time points (1), (2), and (3). Calculated foot wound surface area (FWSA; derived from measurement of wound maximal dimensions across multiple longitudinal, horizontal, and depth axis), character, location, and surrounding tissue will be evaluated(51). This measurement is based on FDA guidance recommendations for trials on wound healing (2006). A digital picture of the wound and its surrounding tissue adjacent to a measurement marker will be obtained and labeled with a de-identified subject study ID number. Wounds will also be graded at each assessment time point using the WIfI scoring system. Comparison of wound healing between time points (1) & (2) will help assess for potential performance bias, as well as determine if wound healing is being affected by altered compliance to standard of care after study enrollment. Comparisons between time points (2) & (3) will help assess extent of wound healing over the study period.

Mobile health technology for FW monitoring will be incorporated to this study to enhance data collection of calculated wound surface area over the course of the study period. Mobile technologies are increasingly used to provide effective strategies to promote patient engagement and compliance. We will utilize a functional wound assessment mobile application (BodyMapSnap) that employs a highly usable, patient-facing dashboard modeled on popular wound care electronic health records (5 star rating).

Additional programming to the mobile application will be made to trigger a prompt for a weekly wound appearance assessment. The day of the prompt will be scheduled at random each week. Participants will be prompted to report if the wound size is "smaller" or "larger," and to log a picture of the wound adjacent to a measuring marker (in centimeters). A "friendly nudge" reminder later in the day will prompt participants who do not immediately respond to the brief weekly assessment. Upon completing the brief assessment, participants will receive a motivational message for their level of adherence. Additionally, the app will include engaging features that are responsive to the participant responses.

Participants that do not have access to iPhone, iPad or internet will still be provided with an app profile that will be updated at time points (1), (2), or (3) using data collected by the participants using a weekly paper book wound diary supplied by the study team. Participants will be asked to record if they believe the wound is "smaller" or "larger," and to take a picture with an adjacent measurement marker using a disposable camera supplied by the study team. Similar to the in-person assessments, the patient's self-reported weekly wound assessments will be used to provide FWSA assessments between study time points (2) & (3), as well as provide overall wound healing trends (improvement or deterioration in healing), drastic changes in the course of healing (shift from improvement to deterioration, or vice versa), and complete healing prior to time point (3).

Serum cFAS assessments will also occur for subjects in both Group 1 & 2 at longitudinal time points (2) & (3) to determine the cFAS variability over time. Participants will be asked to provide a 10 mL fasting blood sample obtained via a peripheral intravenous puncture using a single Red-Top vacutainer tube containing no anticoagulation. Serum will be collected using established Washington University Section of Vascular Surgery serum biobanking protocols.

Total cFAS content will be evaluated using commercially available validated 96-well ELISA (see data above). cFAS enzyme activity will be evaluated using a high throughput 96-well modified NADPH depletion assay as previously described by our group(52, 53). Serum samples (in triplicate) from each patient will be added to an assay buffer, and NADPH oxidation will be initiated by addition of a standard concentration of malonyl-CoA (precursor used by cFAS to catalyze production of palmitic acid (PA)). The reaction rate is determined by monitoring the decrease in NADPH absorbance at 340 nm using a multi-well spectrophotometer.

Quality control (QC) for cFAS content and enzyme activity assessments will be included to evaluate data reproducibility and variance. To achieve this, for each 25 patients a random repeat sample from the same analysis batch, as well as a previous analysis batch, will be included in the current cFAS content/activity assays, and the values obtained for the repeat samples will be compared across experiments. Batches represented by repeat samples with a coefficient of variation (CV) <15% will be considered reliable for subsequent analyses.

Serum FA assessments will occur for Group 1 & 2 at longitudinal time points (2) & (3). Free FAs will be extracted from 50 uL of serum by a modified Bligh-Dyer method. The extraction will be conducted in the presence of synthetic internal standards that do not exist in nature. The extracted free fatty acids will be further derivatized by amino methyl phenyl pyridium (AMPP) into FA-AMPP derivatives in order to obtain high sensitivity with mass spectrometry analysis. The relative quantities of PUFAs and SFAs will be determined using an automated Shimadzu 10A HPLC system and a Shimadzu SIL-20AC HT auto-sampler coupled to a Thermo Scientific TSQ Quantum Ultra triple-quadruple mass spectrometer operated in Selected Reaction Monitoring (SRM) mode under Electrospray Ionization (ESI+). The data will be reported as the m/z peak area ratios of the analytes to the corresponding internal standard. Objective data processing will be conducted using Xcalibur operating system (Thermo). QC assessments will also be integrated into the automated sample analysis. Aliquots from different study samples will be pooled and will be used to inspect instrument accuracy and stability. The QC will be injected six times in the beginning to stabilize the instrument, and will be injected between every 6 study samples. Only the lipid species with a CV <15% in QC sample will be considered to be reliable for subsequent analysis.

Primary Outcome.

We will evaluate the difference in cFAS content between Group 1 & 2 at time point (3).

Secondary Outcomes.

We will evaluate the difference in cFAS enzymatic activity, and change of FWSA (from time point (1) to (3)), between Group 1 & 2. Additionally, we will evaluate whether FWSA and WIfI scores between Group 1 & 2 correlate with cFAS content/activity at time points (2) and (3). Taken together, our outcome measures will help determine whether T2D severity is associated with cFAS content and/or activity.

Exploratory Outcomes.

First, we will evaluate trends in FWSA from self-reported wound assessments. This will help identify potential confounding variables and/or wound care non-compliance issues. Second, we will evaluate the relative abundance of PUFAs and SFAs between Groups 1 & 2, at time points (2) and (3). From this we will explore differences in FAs linked to wound healing (arachidonic acid (AA; 20:4n-6) and eicosapentaenoic acid (EPA; 20:5n-3)), and increased risk of cardiovascular disease (docosahexaenoic acid, DHA). We anticipate these comparisons will also direct additional future biomarker validation (see section 4).

TIMELINE: App customization, system software integration, and IRB approvals will be completed in months 3 to 6. We anticipate that enrollment will begin at 6 months. We plan to enroll 100 patients over 2.5 years at Washington University. Enrollment will conclude at 36 months. Months 36 to 42 will be for data analysis.

STATISTICAL POWER: The null hypothesis is that cFAS content is the same between Groups 1 & 2. Based on our preliminary data, the alternative hypothesis estimates that Group 1 mean (standard deviation; SD)=4.8(2.5), and Group 2 mean(SD)=9.7(3.5). With 250 patients in each group, anticipated dropout rate of 10%, and two-sided significance level of 0.0167, the power is >99% using a two-sample t-test. For adjusted analyses, we will consider 10 additional covariates and a combined covariate-outcome $R^2$ of 0.5, which also provides power >99% using an F test.

Numbers Eligible.

Based on our study inclusion/exclusion criteria, we estimate that >650 adults with T2D and FWs over the past 2.5 years (2015-2017) would have been eligible for this study at Washington University. Thus, we anticipate that we will be able to meet our recruitment target within the allotted timeline.

Statistical Analysis of Data.

Primary outcome analysis will be performed using a two-sample t test to compare mean cFAS content in Group 1 & 2 at time point (3) (assuming cFAS has a normal distribution), or use a non-parametric Wilcoxon to compare the median cFAS content between groups (if the normality assumption is not tenable). We will also use linear regression modeling to compare the mean cFAS content between the groups adjusted for all relevant potential confounding factors (e.g. pertinent demographics, lipid lowering oral medications, using of hyperbaric oxygen therapy (HBO)). In addition, we will evaluate the dependency of difference between the two groups on other variables by testing group-by-variable interaction terms. Secondary outcome analysis will be performed for: 1) cFAS activity, and FWSA, similar to that described for cFAS content above; 2) WIfI score (ordinal variable) correlation with cFAS content, and activity, will be performed using polyserial correlation and Fisher's z transformations. Partial correlation coefficients will be used to adjust for potential confounders (severity of ischemia and/or infection). Exploratory outcome analysis will be performed using a mixed effects regression model with the following specification: $FWSA_{ij} = \gamma_{00} + \gamma_{10}*week_{ij} + \gamma_{01}*group_j + v\gamma_{11}*group_j*week_{ij} + u_{0j} + u_{1j}*week_{ij} + e_{ij}$, where $FWSA_{ij}$ is FWSA measurement at week i for subject j. $\gamma_{00}$ is the mean of FWSA for those in the Group 1 at week 0 (the intercept for the reference group); $\gamma_{01}$ is the difference in the intercepts between the two groups; $\gamma_{10}$ is the slope of week (rate of change) for those in the reference group; $\gamma_{11}$ is the difference in the slopes between the two groups. These parameters are the fixed effects parameters, which allow us to assess the group difference in the longitudinal profiles, and the group difference at a specific week (cross-sectional). $u_{0j}$ is a random deviation of subject j's intercept from his or her group intercept, and $u_{1j}$ is a random deviation of subject j's slope from his or her group slope. These random effects parameters and their empirical Bayes estimates for each subject allows us to assess individual heterogeneity in the longitudinal profiles within each group. In order to adjust for other covariates, we will enter those covariates as the fixed effects into the model. Nonlinear trends can also be accommodated using a higher order polynomial function or spline function for week in this model. This model will be applied using SAS software.

Previous reports, as noted in our data, demonstrate that our outcome measures are adequately sensitive to detect differences in cFAS in subjects with T2D and high/low DCSI. However, in the unlikely event that cFAS is found to not have sufficient sensitivity, we will direct our efforts to evaluate the relative differences in PUFA and SFA between Groups 1 & 2 (as described in the exploratory outcomes section).

FW self-assessments are necessary for providing the type of granular data needed to evaluate our exploratory outcomes (we anticipate that some wounds will increase and some will decrease in size over study period). As such, we will implement technology-driven strategies and health intervention techniques rooted in behavioral science to enhance compliance with patient FW self-assessments. Use of app or wound diary on a weekly basis will hopefully strike the right balance between keeping the participant engaged with the study, and at the same time not become overwhelmed with excessive self-reporting. Nevertheless, we recognize that patients with multiple co-morbidities and health requirements may lead to issues with noncompliance.

The use of electronic media (iPhone, iPad, and internet) may lead to an element of selection bias to individuals who access to this technology. We will make every effort to prevent actual or perceived barriers in recruiting individuals who are less facile with modern electronic devices, or access to the proposed electronic media. To facilitate this we will ensure that study subjects who do not have access to electronic media are instead provided with a personalized wound diary paper book and log. Furthermore, we will utilize existing resources at Washington University, such as the REACH program, to recruit subjects who are uninsured or typically under-represented in clinical trials. We believe this will enhance the generalizability of our study.

We recognize that patient's diet and use of serum lipid altering medications (statins and fibrates) may alter serum cFAS and cFAS activity. We also recognize that the extent of wound healing may be confounded by the level of infection (within the eligible wound classes), and type of wound care dressings used to treat the wound (within the standard of care paradigms(46)). We will evaluate these potential confounding factors in multivariate modeling (described in the statistical analysis).

Inclusion Criteria:
1) Age 18 or above
2) T2D with DCSI (1-10)
3) have a chronic non-healing FW (lasting >1 month)
4) Society for Vascular Surgery (SVS) Wound (W), Ischemia (I), and foot Infection (fi; WIfI score of W≥1, I≤2, and fI≤2)
5) Rutherford Class 1 (mild claudication)-2 (moderate claudication)
6) Are able and willing to receive FW evaluations and treatments per standard of care (e.g. off-loading, debridement, regular dressing changes).

Exclusion Criteria:
1) DCSI ≥11
2) Taking oral dietary fish oil supplements (which are rich in FAs)
3) Taking Cilostazol therapy
4) Have an active cancer or malignancy (which can increase cFAS)
5) Anticipated amputation in the ipsilateral limb within 4 weeks of study enrollment
6) And severe foot wound infection (i.e. purulence, cellulitis, extensive necrosis; WIfI score with fI of 3)

(2) To Investigate the Effect of Cilostazol Therapy on cFAS Biomarker and FW Healing in Patients with High or Low T2D Severity.

Here, we will investigate the effect of Cilostazol therapy on cFAS biomarker and FW healing in patients with high or low DCSI. Cilostazol is the only FDA-approved medication for the treatment of patients with mild-moderate PAD and claudication. Several studies demonstrate off-label benefits of Cilostazol in preventing clinical progression of T2D-associated complications, normalizing serum lipid profiles, and decreasing the incidence of FWs in individuals with T2D. Using a different patient cohort from section 1, we propose another multi-center, prospective, cohort study to determine whether cFAS can monitor the effect of a 4-month course of orally administered Cilostazol therapy on FW healing in subjects with T2D. We will leverage existing wound assessment informatics to facilitate multi-center web and cloud-based data storage and analysis. We will also implement mobile health technologies rooted in behavioral science to maintain a high level of study compliance and medication adherence. We hypothesize that cFAS will be reduced with Cilostazol therapy in both high and low DCSI subjects, and indirectly predictive of wound healing.

Significance: Cilostazol has an Established Benefit in Subjects with PAD.

Cilostazol (Pletal®, OPC-13013, 6-[4-(1-cyclohexyl-1H-tetrazol-5-yl)butoxy]-3,4-dihydrocarbostyril), is an orally administered drug that exerts favorable outcomes on walking distance in patients with claudication. A 3-month treatment course with Cilostazol increases walking distance by 35-50% in patients with claudication—presumably through its antiplatelet and peripheral vascular vasodilatory effects (54, 55). It was FDA approved in 1999, and since then has been widely accepted into the standard of care management of patients with mild to moderate PAD. To date, there are no trials that have evaluated the effect of Cilostazol in patients with T2D and open FWs. Here, we propose a clinical trial to determine whether cFAS and FW healing are altered with Cilostazol therapy.

Cilostazol Improves Serum Lipid Profiles and Clinical Outcomes in Subjects with T2D.

Several large-scale trials have illustrated the off-label benefits of Cilostazol in both prevention and alleviation of T2D-associated complications(56, 57). In a recent meta-analysis of 12 RCTs, Cilostazol was found to significantly decrease the risk of total vascular events, especially cerebrovascular events, in patients with T2D(58). Several additional trials demonstrate that a 3 to 6 month course of Cilostazol therapy can improve pro-atherogenic lipid profiles, and decrease total cholesterol and serum LDL (58, 59). Collectively, these studies demonstrate that Cilostazol has beneficial pleotropic effects that decrease T2D-associated complications, and provide a platform for our hypothesis that Cilostazol can improve T2D-associated FW healing.

Innovation: Cilostazol for Treatment of Subjects with T2D and Open FWs.

Aside from smoking cessation and physical exercise, there are currently no known effective medical treatments to prevent amputations in patients with T2D and FWs(10). We are proposing a clinical trial to evaluate the effect of Cilostazol therapy on cFAS biomarker and FW healing. These studies are highly innovative in that they: 1) Will help evaluate cFAS as an indicative biomarker that can monitor FW healing; 2) Will fill a current void in the potential off-label benefits for Cilostazol in subjects with T2D and open FWs; 3) Explore a highly feasible method of therapy that can be widely adopted among practicing clinicians who normally care for subjects with T2D; and 4) Represent the potential use of a low-cost, generic pharmacological agent, which would otherwise not be pursued by drug pharmaceutical manufacturers due to the anticipated low-profit margins (Cilostazol therapy costs $23.32/month, i.e. 60 tablets)

Mobile Technology Behavioral Health Strategies to Improve Adherence to Cilostazol Intervention.

We will use mobile technologies as a tool to promote patient engagement and adherence to the proposed study treatment(60). In particular, we will use behavioral science methods such as reminder prompts(60), social connectivity (61), and a patient avatar interface(62) as key components to enhance adherence.

Data.

Figures 11A, 11B:
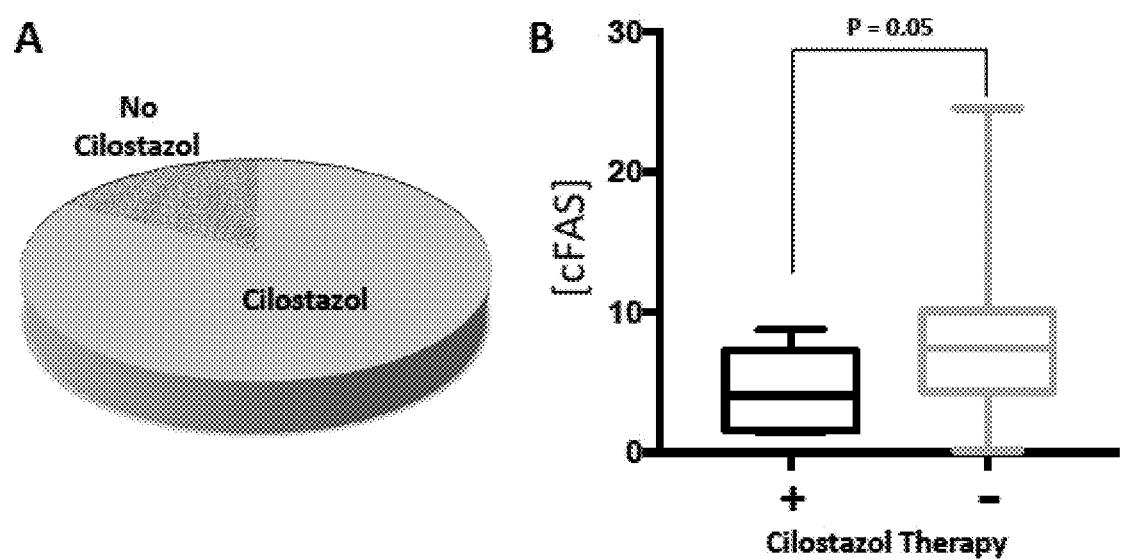
FIG. 11A-FIG. 11B is a pie chart and box plot showing cilostazol in our subjects with T2D and PAD.

We retrospectively reviewed patient encounters at the Barnes-Jewish Hospital vascular surgery clinic over a 6-month period to determine the prevalence of Cilostazol prescriptions among subjects with T2D, PAD and/or FWs. We found that only 18.7% of subjects were prescribed Cilostazol (FIG. 11A). This suggests that the majority of patients with T2D are typically not prescribed Cilostazol, and confirms feasibility in recruiting study subjects who are naive to the medication at the start of the study (see inclusion/exclusion criteria). Additionally, we found that patients with T2D who were taking Cilostazol therapy, cFAS was significantly lower compared to subjects who were not receiving the medication (FIG. 11B). Combined with previous literature demonstrating that Cilostazol can normalize serum lipid profiles(58, 59), and alter PUFA to SFA ratio (63), our data provides additional impetus to explore the effect of Cilostazol on cFAS and serum FAs in a large multi-center trial.

Approach: A Multi-Center, Prospective Trial to Study the Effects of Cilostazol Therapy on cFAS in Subjects with T2D and FWs.

Figure 10:
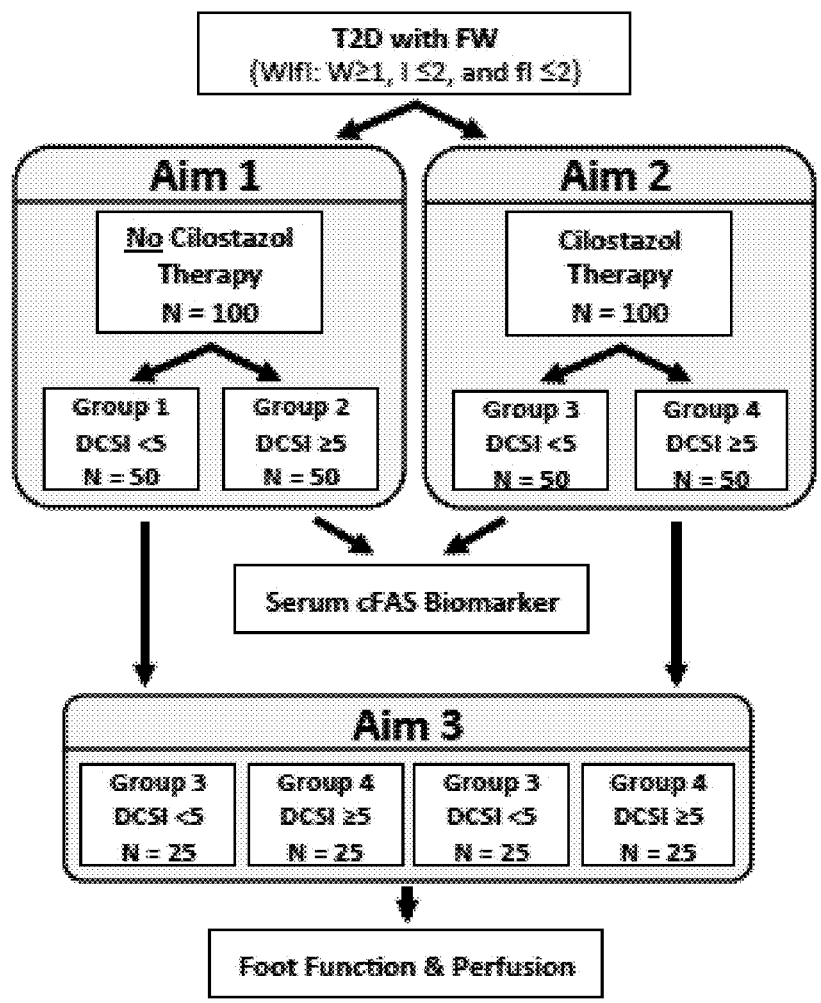
FIG. 10 is a schematic of sections 1, 2, and 3. Number of subjects (N) represents Washington University recruitment goal.

Participants with chronic non-healing open FWs with DCSI <5 (Group 3) and DCSI ≥5 (Group 4) will receive Cilostazol therapy (FIG. 10). Both groups will also receive standard wound care therapy, as well as a run-in period of 2 weeks (10-18 days) where wound care therapy will be implemented. Time point (0) is when the study participant initiates oral administration of the study drug provided by the research pharmacy following enrollment. As prescribed for patients with claudication, Cilostazol will be administered 100 mg, oral tablet, twice daily. The trial duration will be 4 months (120 days from Time 0), with primary and secondary outcome measurements determined at the end of the study period.

Subjects.

We plan to recruit a total of 500 participants. Participant inclusion and exclusion criteria will be the same as outlined in section 1. Additionally, subjects will be excluded if there is evidence of Class III-IV heart failure (since Cilostazol therapy can exacerbate the condition and has an FDA black-box warning in this specific patient population). Participants will also be excluded if they receive medications that have strong interactions with Cilostazol (Omeprazole or CYP2C19/CYP3A4 inhibitors). Patients already taking Cilostazol within the last 6 months will also be excluded from the study.

Assessments.

Baseline evaluation will be performed at study enrollment (time point (1)), and will include an assessment of demographics, medical history, peripheral vascular pulse exam, baseline ankle-brachial index (ABI), toe pressure and toe-brachial index (TBI), and anthropometric measures (including vital signs). Baseline WIfI score will also be calculated for each study subject FW. Cilostazol prescription will be administered by a research pharmacy. Standard FW care will be provided based on the International Best Practice Guidelines for Management of Diabetic Foot Wounds(46). This will include optimal glycemic control, effective local wound care (debridement and dressings), infection control, HBO as clinically indicated, and pressure relieving strategies. Experienced wound care specialists at each participating trial center will be expected to continue to manage participants during the trial period.

In-person FW assessments will be performed 2 weeks following enrollment (trial run-in phase; time point (2)) to assess wound care, initial compliance with Cilostazol, potential medication side effects, provide the participant opportunities to ask questions, and allow for research coordinators to reinforce medication compliance. Afterwards participants will be evaluated monthly for additional in-person FW healing assessments (as described in section 1). At each assessment, FWSA and WIfI score will be obtained.

Mobile health technology and behavioral strategies to improve adherence to Cilostazol intervention will also be implemented as similarly proposed in section 1. Specifically we will also use the mobile application to access both FW healing, as well as adherence to Cilostazol. Participants will be prompted weekly to report if the wound size is "smaller" or "larger," and to log a picture of the FW. Adherence to Cilostazol will also be self-reported by indicating am and pm doses that were taken on a mobile weekly calendar for the previous week. Participants will receive a motivational message for their level of adherence in the previous week.

Grounded in self-perception theory and the Proteus effect (62), the app will also include a virtual self-avatar, unique and customizable to each participant. The avatar will model wound healing in the avatar foot, with an increase or decrease in the size of the wound based on participants' description of the wound appearance and reported adherence to the medication prescription. For instance, the avatar will respond with positive feedback for sustained decrease in wound size from the past week, and adherence to the medication prescription over the past week, and will provide motivational messages for increasing wound size or poor/declining adherence to the study medication (e.g. <80% adherence to the study medication).

Additionally, social connectivity and competition will be leveraged via a leaderboard by indicating the place rank, percentile rank, and overall adherence to the medication prescription (e.g. $10^{th}$ place, $95^{th}$ percentile, 90.2% adherence). Participants will each have a personal username (different from actual names to maintain anonymity and protection of identity), and the top 100 usernames will be displayed on a leaderboard to encourage high adherence. Participants that do not have access to iPhone, iPad or internet, will also be provided with an electronic profile that will be updated at the monthly study visits. Participant will be asked to complete a once a week wound diary assessment, and take a picture with an adjacent measurement marker. This data will be uploaded to the app on a desktop computer during the participant's monthly study visits, and the subject will be able to observe the avatar feedback and leaderboard at these regular visits.

We will assess barriers and facilitators to engagement and adherence, as well as perceptions regarding the adherence strategy. To obtain sufficient variation in responses, we will use intensity sampling to conduct semi-structured qualitative interviews with two groups of participants, those with relatively high and low adherence.

Serum cFAS biomarker and FA assessments will be performed similar to that described in section 1. Subjects in this multi-center trial will be asked to provide a blood sample at time points (2) and (3). Serum cFAS content/activity and FA content will be evaluated.

TABLE 3

Time point analysis of Serum cFAS content/activity and FA content.

| | Time Point (0): | Time Point (1): Baseline after start of Cilostazol | Time Point (2): 2-weeks (run-in phase) | Time Point (3): 4-months following enrollment | Self-Assessments (App): weekly after enrollment |
|---|---|---|---|---|---|
| FWSA | Initiation of Oral Cilostazol Therapy | X | X | X | X |
| WIfI | | X | X | X | X |
| cFAS Content & Activity | | X | | X | |
| Serum FA Content | | | X | | X |

Primary Outcome.

We will evaluate the difference in cFAS content between Group 3 & 4 at time point (3).

Secondary Outcomes.

We will evaluate the difference in cFAS activity, and change in FWSA, between Group 3 & 4 at time point (3). We will also evaluate the difference in FA lipid profiles between Group 3 & 4.

Exploratory Outcomes.

We will perform comparisons between sections 1 and 2, to evaluate the effect of Cilostazol on FWSA between Groups 1 & 3 and Groups 2 & 4.

Safety Monitoring.

Participants will be evaluated initially at 2 weeks following enrollment to assess the patient for any adverse drug reactions, and major/minor side effects. Participants who develops signs of congestive heart failure (chest pain, severe shortness of breath with pulmonary congestion and/or lower extremity edema)(64) will be immediately withdrawn from the study and expert cardiology consultation will be obtained. Minor side effects may including headaches (34%), diarrhea (19%), dizziness (10%), pharyngitis (10%), nausea (7%), dyspepsia (6%), abdominal pain (5%), cough (4%), flatulence (3%), myalgia (3%), vertigo (2%), vomiting (2%), arthritis (2%), and skin rash (2%)(64, 65). Depending on the clinical severity of these findings participants may be withdrawn from the study at the discretion of the study team and/or participant. All subjects who develop minor side effect will be evaluated again within 2 weeks from the start of symptoms. At this point, if the subject's symptoms have progressed, the subject will be withdrawn from the study (if they have not been already withdrawn at the start of initial symptoms) and expert medical consultation will be sought.

Procedures for Withdrawal.

We plan to interview all participants that voluntarily withdraw from the study to determine the reasons for withdrawal. Participants who withdraw will be encouraged to still consider participating in weekly FW assessments to impart as much data as possible.

Timeline.

We anticipate enrollment will begin at 6 months. We plan to enroll 100 participants over 2-3 years at Washington University. Enrollment will conclude at 42 months. Months 42 to 48 will be for data analysis.

Statistical Power.

The null hypothesis is that cFAS content is the same between Groups 3 & 4. Based on our preliminary data, the alternative hypothesis estimates that Group 3 mean(SD)=3.5

(2.0), and Group 4 mean(SD)=7.5(2.5). With 250 patients in each group, anticipated dropout rate of 10%, and two-sided significance level of 0.0167, the power is >99% using a two-sample t-test. For adjusted analysis, we will consider 10 additional covariates and a combined covariate-outcome $R^2$ of 0.5, which will also provide power of >99% using an F test.

Numbers Eligible.

Based on our study inclusion and exclusion criteria, we estimate that >450 adults with T2D and open FWs over the past 2.5 years (2015 to 2017) would have been eligible for this study at Washington University. Thus, we anticipate that we will be able to meet our recruitment target within the allotted study timeline.

Statistical Analysis of Data.

Primary outcome measure will evaluate cFAS content between Group 3 & 4 at time point (3) using the same statistical methods described in section 1 primary outcome measure. Secondary outcome measures will be performed using unadjusted two group comparisons using t-test or non-parametric Wilcoxon tests as appropriate. We will also use multiple linear regression models to adjust for potential relevant confounding variables (as also described in section 1 statistical analysis).

The idea of taking an additional medication twice a day (once in the morning and once in the evening) is challenging for many patients with T2D and FWs. However, prior studies that evaluated the pleotropic effects of Cilostazol in subjects with T2D report >90% drug compliance rates(54, 57, 66, 67). We believe that our regular monthly in-person FW assessments will also provide our study team ample opportunity to encourage patient study compliance. We will further reinforce this with behavioral science techniques through our mobile health technology that is aimed to motivate participants to maintain a high level of interest and study compliance(60).

This can be problematic for our primary and secondary endpoints. Prior studies demonstrate that 3 months of sustained use of Cilostazol is necessary for optimal pharmacological effects(54, 58, 67). Therefore, we will make concerted efforts to communicate regularly with study participants to engender good faith and commitment to the study. Additionally, our study coordinator will engage participants and maintain good rapport via: 1) letters and phone calls to remind participants the importance of completing their weekly FW self-assessments and for taking the study drug; 2) personalized mailings (birthday cards); 3) token incentive gifts (gift cards to recognize important accomplishments in the study); and 4) transportation (parking and gas cards). We anticipate that this personalized approach will maintain high overall protocol adherence.

Section 1 & 2 each outline complementary, yet independent clinical trials that will evaluate cFAS as a biomarker for FW healing. section 1 will characterize cFAS as a diagnostic biomarker, while section 2 will characterize cFAS as an indicative biomarker.

Participant inclusion and exclusion criteria will be the same as outlined in section 1. Additionally, subjects will be excluded if:
1) Evidence of Class III-IV heart failure
2) Receive medications that have a strong interaction with Cilostazol (CYP2C19 or CYP3A4 inhibitors)
3) Patients already taking Cilostazol within the last 6 months (3) To Investigate the Relationship Between cFAS Biomarker, Foot Function, and Skin Perfusion in Patients with T2D and FW Who are Treated with or without Cilostazol.

Here, we will investigate the relationship between cFAS biomarker, foot function, and skin perfusion in patients with T2D and FWs who are treated with or without Cilostazol. Patients with T2D and FWs often have impaired foot function and perfusion. Cilostazol therapy can improve both of these parameters. We, therefore, propose a sub-population assessment of subjects recruited in sections 1 and 2 to determine whether cFAS can predict the level of foot function and skin perfusion in subjects treated with or without Cilostazol. Longitudinal assessments will be performed with validated foot function and skin perfusion assessments, as well as with a novel, institutionally developed, MR technique that evaluates foot skeletal muscle perfusion. We hypothesize that cFAS will correlate with foot function and skin perfusion, and may reflect changes associated with Cilostazol therapy.

Significance: Assessment of Foot Function and Perfusion to Evaluate the Potential Clinical Benefit of Cilostazol.

Previous studies demonstrate that Cilostazol can improve limb function (walking distance)(68), promote wound healing(69, 70), and enhance peripheral skin perfusion(55). An 8-week course of Cilostazol in patients with T2D and PAD, was sufficient in improving lower extremity ischemic symptoms as well as improve peripheral skin perfusion detected with transcutaneous oxygen pressure (TcPO2)(67). Another study demonstrated that Cilostazol therapy can prevent the onset of FWs in patients with T2D(71). To date, there are no studies that evaluate whether Cilostazol can have similar beneficial outcomes in subjects with T2D who already have an open FW. Here, we select subpopulations from sections 1 & 2 to evaluate the relationship between cFAS and clinically relevant endpoints affected by Cilostazol therapy (i.e. function and perfusion). Decreased microvascular perfusion is a major cause of impaired FW healing in subjects with T2D. In response to injury, subjects with T2D have blunted oxygen exchange and vasodilatory response in the peripheral tissue(48). Diabetic neuropathy can exacerbate the condition through arteriovenous shunting(72, 73), which can further impair arterial outflow in the lower leg and foot(74). Dysfunctional regional perfusion in the foot of subjects with T2D is suspected to be the prime contributor to chronic FW formation and impaired healing(75). Options for evaluating local FW bed perfusion are limited, and popular methods mostly evaluate just the macrovascular arterial outflow to the foot. Traditional measures such as ABI/TBI(76), and transcutaneous oxygen pressure (TcPO2) are predictive of wound healing(77-80), but may have limited sensitivity to the microvasculature and deep skeletal muscle perfusion adjacent to the FW(81). Therefore, in addition to conventional methods, we will evaluate the use of multi-modal non-contrast MR as an alternative measure to evaluate the relationship between cFAS and skeletal muscle perfusion, with or without Cilostazol.

Innovation.

This sub-population, cohort study, will be the first to evaluate clinically relevant endpoints of Cilostazol therapy in subjects with T2D and FWs. In addition to evaluating foot function and perfusion using validated clinical techniques, we will also evaluate microvascular perfusion measures using a novel, institutionally developed, non-invasive, non-contrast, MR perfusion technique(82, 83). Assessments will also be made using an MR-compatible foot exercise ergometer(83). This method will provide highly sensitive regional foot skeletal muscle blood flow (SMBF) assessments in areas directly adjacent to the FW. Through prior clinical trials, the necessary infrastructure has been built for this technique and have already validated its use in subjects with T2D and FWs (R01KD105322; see data below).

Data.

Figure 12:
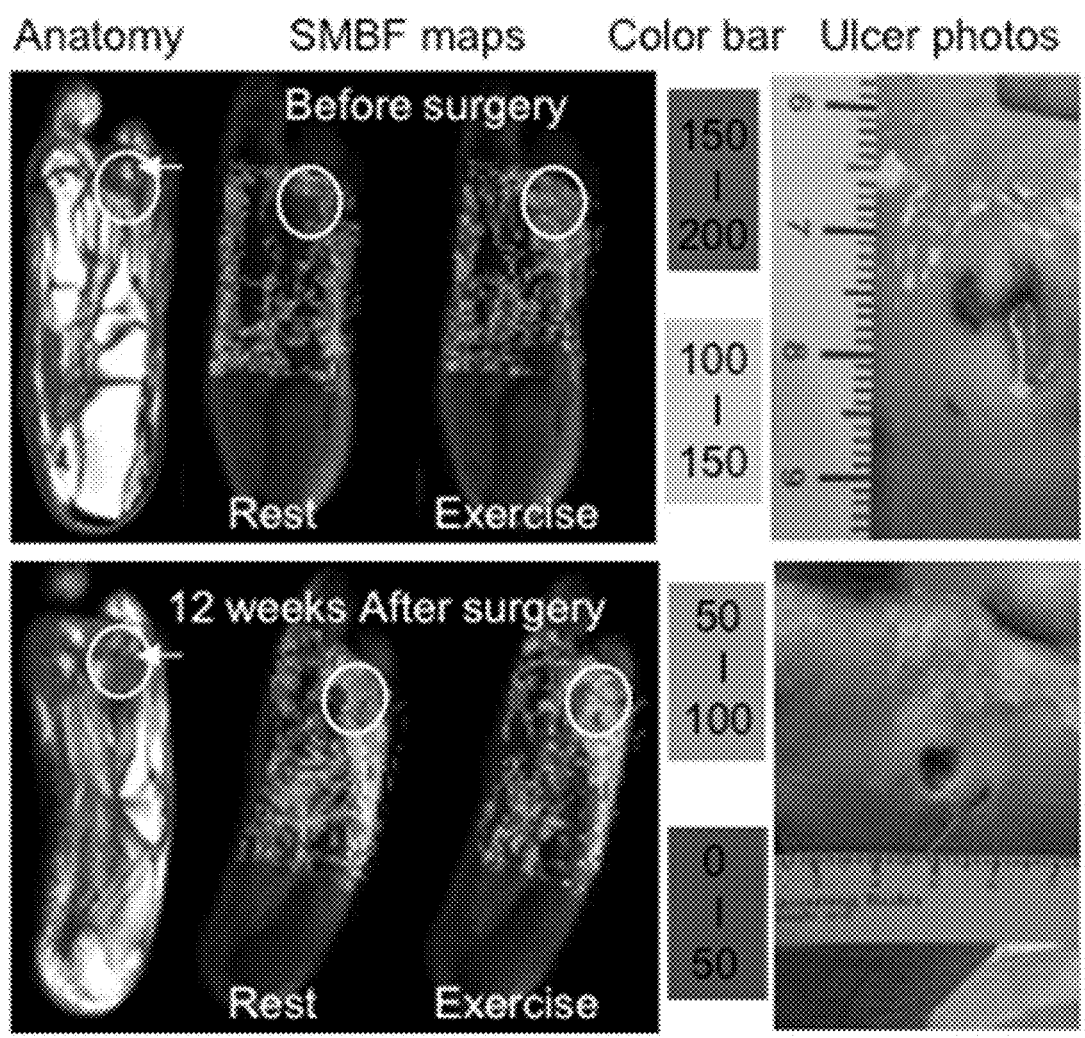
FIG. 12 is a series of MRI images and photos showing regional foot perfusion. Foot MR images before (top) and 12 weeks following revascularization (bottom). Skeletal muscle blood flow (SMBF) maps indicate increased foot perfusion post-exercise following revascularization (color maps displayed in 4 ranges, ml/min/100 g).
Figure 13:
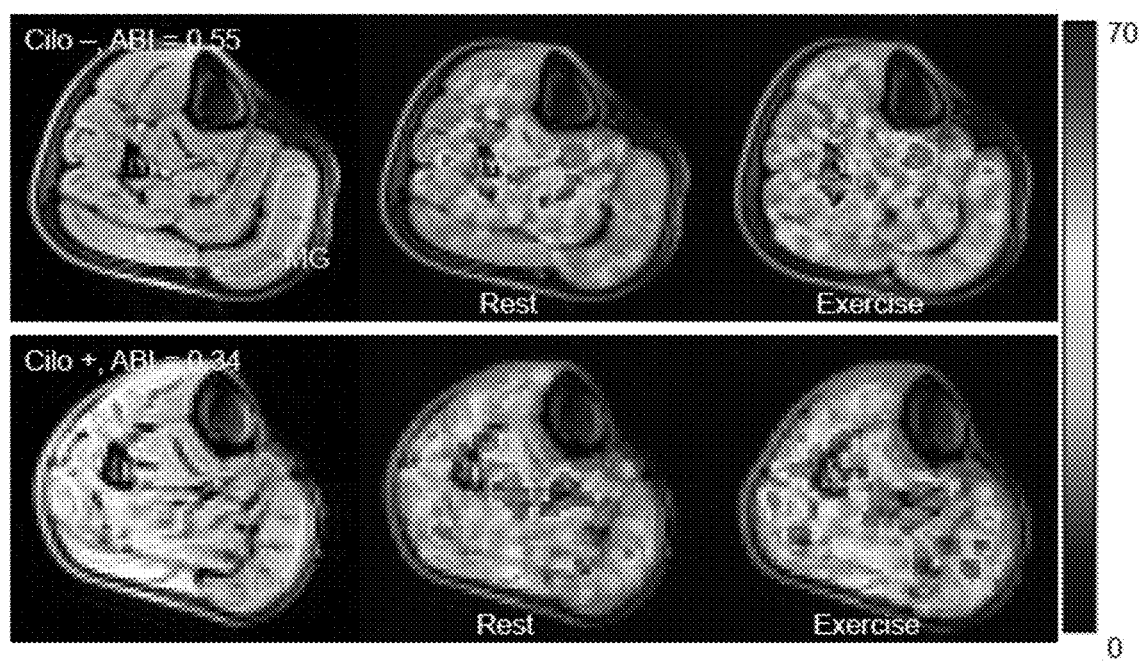
FIG. 13 is a series of MRI images showing comparison of SMBF between subjects with T2D with or without Cilostazol therapy. Subject not treated with Cilostazol (top) demonstrated less lower leg perfusion compared to subject treated with 12 months of Cilostazol (bottom), both at rest and with exercise. MG=Medial Gastrocnemius, SOL=Soleus, color bar unit=ml/min/100 g.

FIG. 12 provides an example of pre- and post-surgical MR-derived SMBF maps that demonstrate improved peri-FW perfusion and associated wound healing. FIG. 13 demonstrates that SMBF is sensitive to detect Cilostazol-induced improved perfusion in critically ischemic limbs (ABI <0.5). These data provide the basis for our hypothesis that in addition to conventional skin perfusion measures (TcPO2), MR-derived SMBF measures with exercise can provide sensitive assessments of deep skeletal muscle perfusion.

Subjects.

We plan to recruit 300 participants (100 subjects from Washington University) from each of the study group (Groups 1, 2, 3, & 4) to receive additional traditional foot functional and perfusion (TcPO2) assessments (FIG. 10). Only subjects recruited at Washington University will also receive MR perfusion assessments (see below). Inclusion and exclusion criteria will be the same as outlined in sections 1 & 2. Additionally, patients who are non-ambulatory >6 months will be excluded from this study. Patients at Washington University with implants that are not compatible with MR will also be excluded.

Assessments.

Foot functional assessments will be performed at time points (1) & (3). As we previously described(84, 85), we will assess ankle plantar flexors using a Biodex multi-joint isokinetic dynamometer at angular velocities of 0°/sec (isometric in neutral ankle position, 0°), and 60°/sec through the available range of ankle motion(86). The ankle flexion angular velocity (AFAV) measure is highly sensitive to deficits in foot skeletal muscle function, which is affected by severity of T2D(87-89). Additionally, we will evaluate lower leg function with a two-minute walk test distance, which is a sensitive indicator of functional mobility(90, 91). We selected these functional assessments to minimize the amount of weight-bearing and adherence to prescribed off-loading restrictions.

Traditional foot perfusion assessments will also be performed at time points (1) & (3) using TcPO2 measurements. We will also obtain standard of care ABI and TBI when applicable.

MR perfusion assessments will only be performed at Washington University, and will also be obtained at the study time points (1) & (3). SMBF measurements in the foot will be obtained (92-94). This will be measured at rest and during a standardized isometric "foot digit flexion, foot crunch" exercise(95, 96). Three-slice SMBF measurements will be acquired at rest and during brief sustained exercise. The image resolution will be 1.6×1.6 mm$^2$ and each slice will need a scan time of 55 seconds. The entire foot imaging study should take no longer than 25 minutes for each study subject. MR perfusion image analysis will be derived from source images from both perfusion and oxygenation measurements. Custom software will be applied for efficient SMBF map analysis. Regions of interest (ROIs) will be outlined on the maps to provide regional data acquisition (FIG. 12). SMBF measurements will be obtained for ROIs at FW site as well as in adjacent areas. The quantities of averaged rest and exercised SMBF for each segment will be measured.

TABLE 4

Assessment Time points.

| Assessments | | Time Point (1): Baseline with or without Cilostazol | Time Point (2): 2-weeks (run-in phase) | Time Point (3): 4-months following enrollment | Self-Assessments (App): weekly after enrollment |
|---|---|---|---|---|---|
| Wound | FWSA | X | X | X | X |
| | Wlfl Score | X | X | X | X |
| Serum | cFAS Content | X | | X | |
| | cFAS Activity | | | | |
| | FA Content | X | | X | |
| Foot Function | AFAV | | X | X | |
| | 2-minute Walk Distance | | X | X | |
| Foot Perfusion | TcPO2 | | X | X | |
| | MR study | | X | X | |

Primary Outcomes.

We will evaluate the change in TcPO2-derived skin perfusion between time points (1) and (3), in Groups 1 versus 3, and Groups 2 versus 4.

Secondary Outcomes.

We will evaluate the change in AFAV and two-minute walk test between Groups 1 & 3, and Groups 2 & 4. Based on our preliminary findings with Cilostazol therapy (FIG. 13), we will also evaluate whether MR-derived SMBF measures correlate with TcPO2 values in Groups 1-4.

Exploratory Outcomes.

We will evaluate whether cFAS content/activity correlates with functional and perfusion measurements in patients with T2D and FWs.

Timeline.

Since patients enrolled in this study will be derived from trials in sections 1 & 2, we anticipate that enrollment in this sub-population cohort study will follow the same recruitment timelines. Enrollment in all studies will conclude at 42 months, and months 42 to 48 will be used for data closeout and analysis.

Statistical Power & Analysis.

Statistical power calculation assumes that the null hypothesis of mean change in TcPO2 is the same in Groups 1 & 3. Based on Zhang et al. (67) the alternative hypothesis estimates a mean change of 4.9 in Group 3. SD of TcPO2 change is estimated at 11.0 in Group 1 and 9.7 in Group 3. With 150 patients in each group and 2-sided 0.016 significance level, the power is >93% using 2-sample t-test. For adjusted analysis, we will consider 10 covariates with a combined covariate-outcome $R^2$=0.5, which also provides a power of >99% using F test. Since the change in TcPO2 is estimated to be the same in Groups 2 & 4, the power for comparing these groups should be similar. Primary outcome measures will be evaluated by calculating changes in TcPO2 between time points (1) and (3) for each study participant.

Changes in TcPO2 will be compared using unadjusted t-test or non-parametric Wilcoxon test as appropriate. A multiple linear regression model will be used to adjust for potential relevant confounding variables. We can combine all patients from Groups 1-4 into one model to increase statistical efficacy and use appropriate contrast when performing comparisons between Group 1 & 3, and Group 2 & 4. Secondary outcome measures of change in AFAV, two-minute walk distance, and exercise SMBF will be performed similar to the primary outcome measure. Exploratory outcome measures will be determined by using a multiple regression analysis to measure correlation coefficients for the change in cFAS content and activity, TcPO2, AFAV, two-minute walk distance, and SMBF between Group 1 & 3, and Group 2 & 4.

We acknowledge that some subjects may have difficulty with physical activities associated with proposed functional and MR perfusion assessment. We have validated the use of the proposed functional endpoints in patients with and without foot wounds(84, 85). We have already successfully tested and implemented the proposed perfusion protocol in a number of patients with T2D with and without FWs(82, 83). In over 60 study subjects, completion of the exercise component of the study has been 100%. We believe that our high success in function and perfusion assessments is facilitated by: 1) Detailed explanations with the participant about study expectations; 2) Motivational speech and encouragements to the participant during the testing period; and 3) Abbreviated testing protocols that are not time consuming (<30 minutes total). Nevertheless, we anticipate that a minority of patients may not be able to complete the exercise component of the assessments, and in these patients we will still have the opportunity to at least explore the relationship between cFAS and perfusion measures at rest.

Participant inclusion and exclusion criteria will be the same as outlined in section 1 and section 2. Additionally, subjects will be excluded if:

1) Participants who are non-ambulatory for >6 months
2) Implants that are not compatible with MRI (only at Washington University since MRI will only be performed at this trial site).

(4) Establish a Biorepository that Combines Patient Demographics, Digital FW Assessments, and Serum Biospecimen Data to Support Future Multi-Center Translational Research.

Here, we will establish a biorepository of samples derived from patients with T2D and open FWs for future multi-center translational research studies. The lack of a national biorepository dedicated for patients with T2D and FWs is a critical barrier to translational research, biomarker validation, and treatment discovery. Our group has been very successful in collecting biospecimens and has the capacity to combine clinical data with metadata. We will modify our existing infrastructure to include specimens collected from the studies proposed above, as well as from other key patient groups. An electronic FASCD Study bioinformatics pipeline will integrate digital FW assessments, clinical outcomes, patient specimens, and lipidomic/metabolomics. This resource will be shared with NIDDK data repository and will serve as a foundation for future translational disease to alleviate suffering in patients with T2D and FWs.

This section will integrate data collected in sections 1-3, and may also collect data from patients with T2D and FWs who do not meet trial inclusion/exclusion criteria of the prior sections.

Significance.

The use of a consortium-organized biorepository is immensely beneficial in integrating biospecimens, clinical data, and metadata to accelerate translational research and treatment discovery(97-100). There is currently a lack of such registry dedicated for translational investigation of T2D-associated FWs.

Innovation.

We propose to create a collection of clinical bio-specimens from key populations of patients who have T2D and FWs, and establish an informatics pipeline for integrating patient demographics, specimen, and biochemical/molecular data.

Data.

Figure 14A:
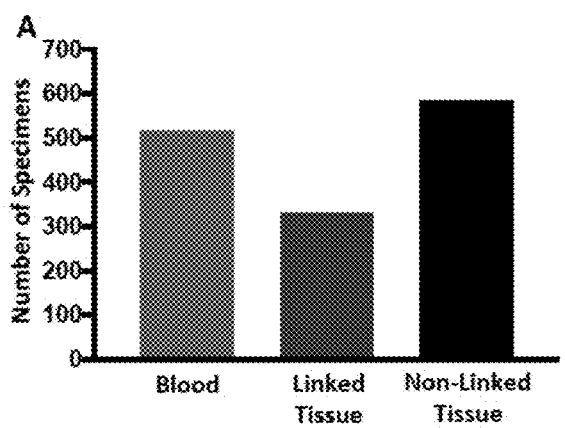
FIG. 14A-FIG. 14B is a series of bar graphs showing bio-specimens collected by existing Vascular Surgery Biobank, 2015-2017.
Figure 14B:
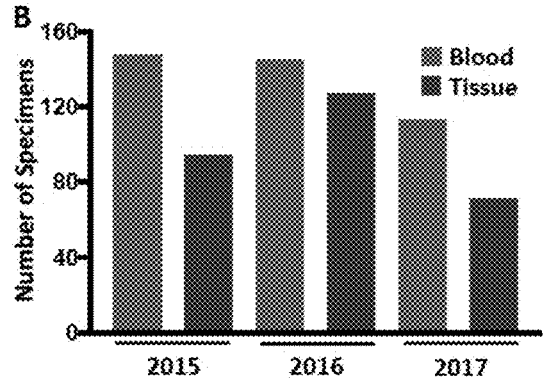

Washington University Vascular Surgery has been very successful in collecting and processing bio-specimens for many studies and clinical trials. Over the past decade we have collected >10,000 specimens that include blood/serum/plasma, arteries, veins, and plaque segments (FIG. 14A). We have a fully functional, IRB approved, biobank protocol that also facilitates collection of 42 clinical variables that include past medical/surgical history, medications, fasting laboratory values, and co-morbidities (FIG. 14B).

Approach.

With modification of the existing Washington University infrastructure, the proposed biorepository will integrate a diverse collection of specimens (e.g. blood/serum/plasma, vessels, adipose tissue, muscle, FW fluid), along with digital FWs picture data, clinical demographic data, and serum lipidomic/metabolomics metadata. This will be collected into the electronic FASCD Study portal, and transferred to NIDDK data repository at set timelines following study closeout. The FASCD Study portal will adhere to standards recommended by the International Clinical Data Interchange Standards Consortium, and will become a resource that maximizes the number of future research directions pursued by Diabetic Foot Consortium investigators. Patients recruited to this biorepository will include participants from clinical trials proposed in sections 1-3, as well as patients with T2D and FWs who did not meet study inclusion/exclusion criteria of proposed trials (e.g. patients with severely ischemic or infected FWs that did not meet study inclusion/exclusion). This strategy will yield a significant number of specimens (estimated >2,500 specimens across 3-5 trial sites), and greatly align institutional resources. Washington University will use this resource to further validate cFAS and serum FA lipidomics as predictive, diagnostic, and indicative biomarkers in specific patient groups, such as: 1) Individuals with high or low cardiovascular morbidities; 2) Specific racial/ethnic groups; 3) Broader FW subtypes (with ischemia and infection); and 4) The effect of adjunct wound therapies such as HBO.

REFERENCES

1. Boulton A J, Vileikyte L, Ragnarson-Tennvall G, Apelqvist J. The global burden of diabetic foot disease. Lancet. 2005; 366(9498):1719-24. doi: 10.1016/S0140-6736(05)67698-2. PubMed PMID: 16291066.
2. Shaw J E, Sicree R A, Zimmet P Z. Global estimates of the prevalence of diabetes for 2010 and 2030. Diabetes Res Clin Pract. 2010; 87(1):4-14. doi: 10.1016/j.diabres.2009.10.007. PubMed PMID: 19896746.
3. National Diabetes Statistics Report, 2017. Available
4. Boyle J P, Thompson T J, Gregg E W, Barker L E, Williamson D F. Projection of the year 2050 burden of diabetes in the US adult population: dynamic modeling of incidence, mortality, and prediabetes prevalence. Popul Health Metr. 2010; 8:29. doi: 10.1186/1478-7954-8-29. PubMed PMID: 20969750; PMCID: PMC2984379.
5. Singh N, Armstrong D G, Lipsky B A. Preventing foot ulcers in patients with diabetes. JAMA. 2005; 293(2): 217-28. doi: 10.1001/jama.293.2.217. PubMed PMID: 15644549.
6. Centers for Disease Control Diabetes in Managed Care Work G. Diabetes mellitus in managed care: complications and resource utilization. Am J Manag Care. 2001; 7(5):501-8. PubMed PMID: 11388129.
7. Ramsey S D, Newton K, Blough D, McCulloch D K, Sandhu N, Wagner E H. Patient-level estimates of the cost of complications in diabetes in a managed-care population. Pharmacoeconomics. 1999; 16(3):285-95. PubMed PMID: 10558040.
8. Nather A, Bee C S, Huak C Y, Chew J L, Lin C B, Neo S, Sim E Y. Epidemiology of diabetic foot problems and predictive factors for limb loss. J Diabetes Complications. 2008; 22(2):77-82. doi: 10.1016/j.jdiacomp.2007.04.004. PubMed PMID: 18280436.
9. Pecoraro R E, Reiber G E, Burgess E M. Pathways to diabetic limb amputation. Basis for prevention. Diabetes Care. 1990; 13(5):513-21. PubMed PMID: 2351029.
10. Beckman J A, Creager M A, Libby P. Diabetes and atherosclerosis: epidemiology, pathophysiology, and management. JAMA. 2002; 287(19):2570-81. PubMed PMID: 12020339.
11. Gregg E W, Li Y, Wang J, Burrows N R, Ali M K, Rolka D, Williams D E, Geiss L. Changes in diabetes-related complications in the United States, 1990-2010. N Engl J Med. 2014; 370(16):1514-23. doi: 10.1056/NEJMoa1310799. PubMed PMID: 24738668.
12. Apelqvist J, Elgzyri T, Larsson J, Londahl M, Nyberg P, Thorne J. Factors related to outcome of neuroischemic/ ischemic foot ulcer in diabetic patients. J Vasc Surg. 2011; 53(6):1582-8 e2. doi: 10.1016/j.jvs.2011.02.006. PubMed PMID: 21515021.
13. Grunfeld C. Diabetic foot ulcers: etiology, treatment, and prevention. Adv Intern Med. 1992; 37:103-32. PubMed PMID: 1557993.
14. Arora S, Pomposelli F, LoGerfo F W, Veves A. Cutaneous microcirculation in the neuropathic diabetic foot improves significantly but not completely after successful lower extremity revascularization. J Vasc Surg. 2002; 35(3):501-5. PubMed PMID: 11877698.
15. Lindley L E, Stojadinovic O, Pastar I, Tomic-Canic M. Biology and Biomarkers for Wound Healing. Plast Reconstr Surg. 2016; 138(3 Suppl):18S-28S. doi: 10.1097/PRS.0000000000002682. PubMed PMID: 27556760; PMCID: PMC4998971.
16. Elraiyah T, Tsapas A, Prutsky G, Domecq J P, Hasan R, Firwana B, Nabhan M, Prokop L, Hingorani A, Claus P L, Steinkraus L W, Murad M H. A systematic review and meta-analysis of adjunctive therapies in diabetic foot ulcers. J Vasc Surg. 2016; 63(2 Suppl):46S-58S e1-2. doi: 10.1016/j.jvs.2015.10.007. PubMed PMID: 26804368.
17. Armstrong D G, Lavery L A, Vela S A, Quebedeaux T L, Fleischli J G. Choosing a practical screening instrument to identify patients at risk for diabetic foot ulceration. Arch Intern Med. 1998; 158(3):289-92. PubMed PMID: 9472210.
18. Young B A, Lin E, Von Korff M, Simon G, Ciechanowski P, Ludman E J, Everson-Stewart S, Kinder L, Oliver M, Boyko E J, Katon W J. Diabetes complications severity index and risk of mortality, hospitalization, and healthcare utilization. Am J Manag Care. 2008; 14(1):15-23. PubMed PMID: 18197741; PMCID: PMC3810070.
19. Clarke P M, Gray A M, Briggs A, Farmer A J, Fenn P, Stevens R J, Matthews D R, Stratton I M, Holman R R, Group UKPDS. A model to estimate the lifetime health outcomes of patients with type 2 diabetes: the United Kingdom Prospective Diabetes Study (UKPDS) Outcomes Model (UKPDS no. 68). Diabetologia. 2004; 47(10): 1747-59. doi: 10.1007/s00125-004-1527-z. PubMed PMID: 15517152.
20. Abbott R D, Donahue R P, Kannel W B, Wilson P W. The impact of diabetes on survival following myocardial infarction in men vs women. The Framingham Study. JAMA. 1988; 260(23):3456-60. PubMed PMID: 2974889.
21. Rosenzweig J L, Weinger K, Poirier-Solomon L, Rushton M. Use of a disease severity index for evaluation of healthcare costs and management of comorbidities of patients with diabetes mellitus. Am J Manag Care. 2002; 8(11):950-8. PubMed PMID: 12437310.
22. Pantalone K M, Misra-Hebert A D, Hobbs T M, Wells B J, Kong S X, Chagin K, Dey T, Milinovich A, Weng W, Bauman J M, Burguera B, Zimmerman R S, Kattan M W. Effect of glycemic control on the Diabetes Complications Severity Index score and development of complications in people with newly diagnosed type 2 diabetes. J Diabetes. 2017. doi: 10.1111/1753-0407.12613. PubMed PMID: 28976724.
23. Itoh Y, Kawamata Y, Harada M, Kobayashi M, Fujii R, Fukusumi S, Ogi K, Hosoya M, Tanaka Y, Uejima H, Tanaka H, Maruyama M, Satoh R, Okubo S, Kizawa H, Komatsu H, Matsumura F, Noguchi Y, Shinohara T, Hinuma S, Fujisawa Y, Fujino M. Free fatty acids regulate insulin secretion from pancreatic beta cells through GPR40. Nature. 2003; 422(6928):173-6. doi: 10.1038/nature01478. PubMed PMID: 12629551.
24. Lovejoy J C, Smith S R, Champagne C M, Most M M, Lefevre M, DeLany J P, Denkins Y M, Rood J C, Veldhuis J, Bray G A. Effects of diets enriched in saturated (palmitic), monounsaturated (oleic), or trans (elaidic) fatty acids on insulin sensitivity and substrate oxidation in healthy adults. Diabetes Care. 2002; 25(8):1283-8. PubMed PMID: 12145222.
25. Mostad I L, Bjerve K S, Bjorgaas M R, Lydersen S, Grill V. Effects of n-3 fatty acids in subjects with type 2 diabetes: reduction of insulin sensitivity and time-dependent alteration from carbohydrate to fat oxidation. Am J Clin Nutr. 2006; 84(3):540-50. PubMed PMID: 16960167.
26. Hodson L, Skeaff C M, Fielding B A. Fatty acid composition of adipose tissue and blood in humans and its use as a biomarker of dietary intake. Prog Lipid Res. 2008; 47(5):348-80. doi: 10.1016/j.plipres.2008.03.003. PubMed PMID: 18435934.
27. Petersson H, Lind L, Hulthe J, Elmgren A, Cederholm T, Riserus U. Relationships between serum fatty acid composition and multiple markers of inflammation and endothelial function in an elderly population. Atherosclerosis. 2009; 203(1):298-303. doi: 10.1016/j.atherosclerosis.2008.06.020. PubMed PMID: 18687433.
28. Wang L, Folsom A R, Zheng Z J, Pankow J S, Eckfeldt J H, Investigators A S. Plasma fatty acid composition and incidence of diabetes in middle-aged adults: the Atherosclerosis Risk in Communities (ARIC) Study. Am J Clin Nutr. 2003; 78(1):91-8. PubMed PMID: 12816776.
29. Corpeleijn E, Feskens E J, Jansen E H, Mensink M, Saris W H, de Bruin T W, Blaak E E. Improvements in glucose tolerance and insulin sensitivity after lifestyle intervention are related to changes in serum fatty acid profile and desaturase activities: the SLIM study. Diabetologia. 2006; 49(10):2392-401. doi: 10.1007/s00125-006-0383-4. PubMed PMID: 16896932.
30. Vessby B, Uusitupa M, Hermansen K, Riccardi G, Rivellese A A, Tapsell L C, Nalsen C, Berglund L, Louheranta A, Rasmussen B M, Calvert G D, Maffetone A, Pedersen E, Gustafsson I B, Storlien L H, Study K. Substituting dietary saturated for monounsaturated fat 31. Erkkila A, de Mello V D, Riserus U, Laaksonen D E. Dietary fatty acids and cardiovascular disease: an epidemiological approach. Prog Lipid Res. 2008; 47(3):172-87. doi: 10.1016/j.plipres.2008.01.004. PubMed PMID: 18328267.
32. Rioux V, Legrand P. Saturated fatty acids: simple molecular structures with complex cellular functions. Curr Opin Clin Nutr Metab Care. 2007; 10(6):752-8. doi: 10.1097/MCO.0b013e3282f01a75. PubMed PMID: 18089958.
33. Jensen-Urstad A P, Semenkovich C F. Fatty acid synthase and liver triglyceride metabolism: housekeeper or messenger? Biochim Biophys Acta. 2012; 1821 (5):747-53. doi: 10.1016/j.bbalip.2011.09.017. PubMed PMID: 22009142; PMCID: PMC3288544.
34. Wakil S J. Fatty acid synthase, a proficient multifunctional enzyme. Biochemistry. 1989; 28(11):4523-30. PubMed PMID: 2669958.
35. Berndt J, Kovacs P, Ruschke K, Kloting N, Fasshauer M, Schon M R, Korner A, Stumvoll M, Bluher M. Fatty acid synthase gene expression in human adipose tissue: association with obesity and type 2 diabetes. Diabetologia. 2007; 50(7):1472-80. doi: 10.1007/s00125-007-0689-x. PubMed PMID: 17492427.
36. Wang Y, Jones Voy B, Urs S, Kim S, Soltani-Bejnood M, Quigley N, Heo Y R, Standridge M, Andersen B, Dhar M, Joshi R, Wortman P, Taylor J W, Chun J, Leuze M, Claycombe K, Saxton A M, Moustaid-Moussa N. The human fatty acid synthase gene and de novo lipogenesis are coordinately regulated in human adipose tissue. J Nutr. 2004; 134(5):1032-8. PubMed PMID: 15113941.
37. Menendez J A, Vazquez-Martin A, Ortega F J, Fernandez-Real J M. Fatty acid synthase: association with insulin resistance, type 2 diabetes, and cancer. Clin Chem. 2009; 55(3):425-38. doi: 10.1373/clinchem.2008.115352. PubMed PMID: 19181734.
38. Wang Y Y, Kuhajda F P, Cheng P, Chee W Y, Li T, Helzlsouer K J, Sokoll L J, Chan D W. A new model ELISA, based on two monoclonal antibodies, for quantification of fatty acid synthase. J Immunoassay Immunochem. 2002; 23(3):279-92. doi: 10.1081/IAS-120013027. PubMed PMID: 12227415.
39. Wang Y, Kuhajda F P, Li J N, Pizer E S, Han W F, Sokoll L J, Chan D W. Fatty acid synthase (FAS) expression in human breast cancer cell culture supernatants and in breast cancer patients. Cancer Lett. 2001; 167(1):99-104. PubMed PMID: 11323104.
40. Wang Y Y, Kuhajda F P, Li J, Finch T T, Cheng P, Koh C, Li T, Sokoll L J, Chan D W. Fatty acid synthase as a tumor marker: its extracellular expression in human breast cancer. J Exp Ther Oncol. 2004; 4(2):101-10. PubMed PMID: 15500005.
41. Zock P L, Mensink R P, Harryvan J, de Vries J H, Katan M B. Fatty acids in serum cholesteryl esters as quantitative biomarkers of dietary intake in humans. Am J Epidemiol. 1997; 145(12):1114-22. PubMed PMID: 9199541.
42. Tavazzi L, Maggioni A P, Marchioli R, Barlera S, Franzosi M G, Latini R, Lucci D, Nicolosi G L, Porcu M, Tognoni G, Gissi H F I. Effect of n-3 polyunsaturated fatty acids in patients with chronic heart failure (the GISSI-HF trial): a randomised, double-blind, placebo-controlled trial. Lancet. 2008; 372(9645):1223-30. doi: 10.1016/S0140-6736(08)61239-8. PubMed PMID: 18757090.
43. Yokoyama M, Origasa H, Matsuzaki M, Matsuzawa Y, Saito Y, Ishikawa Y, Oikawa S, Sasaki J, Hishida H, Itakura H, Kita T, Kitabatake A, Nakaya N, Sakata T, Shimada K, Shirato K, Japan EPAlisl. Effects of eicosapentaenoic acid on major coronary events in hypercholesterolaemic patients (JELIS): a randomised open-label, blinded endpoint analysis. Lancet. 2007; 369(9567): 1090-8. doi: 10.1016/S0140-6736(07)60527-3. PubMed PMID: 17398308.
44. Kumar S, Nilsen W J, Abernethy A, Atienza A, Patrick K, Pavel M, Riley W T, Shar A, Spring B, Spruijt-Metz D, Hedeker D, Honavar V, Kravitz R, Lefebvre R C, Mohr D C, Murphy S A, Quinn C, Shusterman V, Swendeman D. Mobile health technology evaluation: the mHealth evidence workshop. Am J Prev Med. 2013; 45(2):228-36. doi: 10.1016/j.amepre.2013.03.017. PubMed PMID: 23867031; PMCID: PMC3803146.
45. Mills J L, Sr., Conte M S, Armstrong D G, Pomposelli F B, Schanzer A, Sidawy A N, Andros G, Society for Vascular Surgery Lower Extremity Guidelines C. The Society for Vascular Surgery Lower Extremity Threatened Limb Classification System: risk stratification based on wound, ischemia, and foot infection (WIfI). J Vasc Surg. 2014; 59(1):220-34 e1-2. doi: 10.1016/j.jvs.2013.08.003. PubMed PMID: 24126108.
46. American Diabetes A. Consensus Development Conference on Diabetic Foot Wound Care: 7-8 Apr. 1999, Boston, Mass. American Diabetes Association. Diabetes Care. 1999; 22(8):1354-60. PubMed PMID: 10480782.
47. Eneroth M, Larsson J, Apelqvist J. Deep foot infections in patients with diabetes and foot ulcer: an entity with different characteristics, treatments, and prognosis. J Diabetes Complications. 1999; 13(5-6):254-63. PubMed PMID: 10764999.
48. Chao C Y, Cheing G L. Microvascular dysfunction in diabetic foot disease and ulceration. Diabetes Metab Res Rev. 2009; 25(7):604-14. doi: 10.1002/dmrr.1004. PubMed PMID: 19681035.
49. Selby J V, Zhang D. Risk factors for lower extremity amputation in persons with diabetes. Diabetes Care. 1995; 18(4):509-16. PubMed PMID: 7497861.
50. Forsythe R O, Brownrigg J, Hinchliffe R J. Peripheral arterial disease and revascularization of the diabetic foot. Diabetes Obes Metab. 2015; 17(5):435-44. doi: 10.1111/dom.12422. PubMed PMID: 25469642.
51. Commean P K, Mueller M J, Smith K E, Hastings M, Klaesner J, Pilgram T, Robertson D D. Reliability and validity of combined imaging and pressures assessment methods for diabetic feet. Arch Phys Med Rehabil. 2002; 83(4):497-505. PubMed PMID: 11932851.
52. Wei X, Song H, Yin L, Rizzo M G, Sidhu R, Covey D F, Ory D S, Semenkovich C F. Fatty acid synthesis configures the plasma membrane for inflammation in diabetes. Nature. 2016; 539(7628):294-8. doi: 10.1038/nature20117. PubMed PMID: 27806377; PMCID: PMC5671339.
53. Razani B, Zhang H, Schulze P C, Schilling J D, Verbsky J, Lodhi I J, Topkara V K, Feng C, Coleman T, Kovacs A, Kelly D P, Saffitz J E, Dorn G W, 2nd, Nichols C G, Semenkovich C F. Fatty acid synthase modulates homeostatic responses to myocardial stress. J Biol Chem. 2011; 286(35):30949-61. doi: 10.1074/jbc.M111.230508. PubMed PMID: 21757749; PMCID: PMC3162454.
54. Dawson D L, Cutler B S, Meissner M H, Strandness D E, Jr. Cilostazol has beneficial effects in treatment of intermittent claudication: results from a multicenter, ran- 55. Miyashita Y, Saito S, Miyamoto A, Iida O, Nanto S. Cilostazol increases skin perfusion pressure in severely ischemic limbs. Angiology. 2011; 62(1):15-7. doi: 10.1177/0003319710371619. PubMed PMID: 20504836.

56. Asal N J, Wojciak K A. Effect of cilostazol in treating diabetes-associated microvascular complications. Endocrine. 2017; 56(2):240-4. doi: 10.1007/s12020-017-1279-4. PubMed PMID: 28293857.

57. Tang W H, Lin F H, Lee C H, Kuo F C, Hsieh C H, Hsiao F C, Hung Y J. Cilostazol effectively attenuates deterioration of albuminuria in patients with type 2 diabetes: a randomized, placebo-controlled trial. Endocrine. 2014; 45(2):293-301. doi: 10.1007/s12020-013-0002-3. PubMed PMID: 23775007.

58. Geng D F, Deng J, Jin D M, Wu W, Wang J F. Effect of cilostazol on the progression of carotid intima-media thickness: a meta-analysis of randomized controlled trials. Atherosclerosis. 2012; 220(1):177-83. doi: 10.1016/j.atherosclerosis.2011.09.048. PubMed PMID: 22015232.

59. Katakami N, Kim Y S, Kawamori R, Yamasaki Y. The phosphodiesterase inhibitor cilostazol induces regression of carotid atherosclerosis in subjects with type 2 diabetes mellitus: principal results of the Diabetic Atherosclerosis Prevention by Cilostazol (DAPC) study: a randomized trial. Circulation. 2010; 121 (23):2584-91. doi: 10.1161/CIRCULATIONAHA.109.892414. PubMed PMID: 20516379.

60. Alkhaldi G, Hamilton F L, Lau R, Webster R, Michie S, Murray E. The effectiveness of technology-based strategies to promote engagement with digital interventions: a systematic review protocol. JMIR Res Protoc. 2015; 4(2):e47. doi: 10.2196/resprot.3990. PubMed PMID: 25921274; PMCID: PMC4429223.

61. Naslund J A, Aschbrenner K A, Barre L K, Bartels S J. Feasibility of popular m-health technologies for activity tracking among individuals with serious mental illness. Telemed J E Health. 2015; 21(3):213-6. doi: 10.1089/tmj.2014.0105. PubMed PMID: 25536190; PMCID: PMC4365437.

62. Gabarron E, Serrano J A, Wynn R, Armayones M. Avatars using computer/smartphone mediated communication and social networking in prevention of sexually transmitted diseases among North-Norwegian youngsters. BMC Med Inform Decis Mak. 2012; 12:120. doi: 10.1186/1472-6947-12-120. PubMed PMID: 23110684; PMCID: PMC3536646.

63. Nakamura N, Hamazaki T, Johkaji H, Minami S, Yamazaki K, Satoh A, Sawazaki S, Urakaze M, Kobayashi M, Osawa H, Yamabe H, Okomura K. Effects of cilostazol on serum lipid concentrations and plasma fatty acid composition in type 2 diabetic patients with peripheral vascular disease. Clin Exp Med. 2003; 2(4):180-4. doi: 10.1007/s102380300004. PubMed PMID: 12624709.

64. Pratt C M. Analysis of the cilostazol safety database. Am J Cardiol. 2001; 87(12A):28D-33D. PubMed PMID: 11434897.

65. Niki T, Mori H. Phase I study of cilostazol. Safety evaluation at increasing single doses in healthy volunteers. Arzneimittelforschung. 1985; 35(7A):1173-85. PubMed PMID: 4074430.

66. Rosales R L, Santos M M, Mercado-Asis L B. Cilostazol: a pilot study on safety and clinical efficacy in neuropathies of diabetes mellitus type 2 (ASCEND). Angiology. 2011; 62(8):625-35. doi: 10.1177/0003319711410594. PubMed PMID: 21733952.

67. Zhang J, Xiao Z, Chen L, Li L, Yang H, Luo B, Mai L, Yan L, Yang C. Cilostazol Can Increase Skin Oxygen Supply Assessed by Transcutaneous Oxygen Pressure Measurement in Type 2 Diabetes With Lower Limb Ischemic Disease: A Randomized Trial. J Wound Ostomy Continence Nurs. 2016; 43(3):254-9. doi: 10.1097/WON.0000000000000214. PubMed PMID: 26938333.

68. Money S R, Herd J A, Isaacsohn J L, Davidson M, Cutler B, Heckman J, Forbes W P. Effect of cilostazol on walking distances in patients with intermittent claudication caused by peripheral vascular disease. J Vasc Surg. 1998; 27(2): 267-74; discussion 74-5. PubMed PMID: 9510281.

69. Resnick K A, Gordon I L. Effects of cilostazol on arterial wound healing: a retrospective analysis. Ann Vasc Surg. 2014; 28(6):1513-21. doi: 10.1016/j.avsg.2014.02.018. PubMed PMID: 24561209.

70. Zolli A. Foot ulceration due to arterial insufficiency: role of cilostazol. J Wound Care. 2004; 13(2):45-7. doi: 10.12968/jowc.2004.13.2.26580. PubMed PMID: 14999987.

71. de Franciscis S, Gallelli L, Battaglia L, Molinari V, Montemurro R, Stillitano D M, Buffone G, Serra R. Cilostazol prevents foot ulcers in diabetic patients with peripheral vascular disease. Int Wound J. 2015; 12(3): 250-3. doi: 10.1111/iwj.12085. PubMed PMID: 23672237.

72. Krishnan S T, Baker N R, Carrington A L, Rayman G. Comparative roles of microvascular and nerve function in foot ulceration in type 2 diabetes. Diabetes Care. 2004; 27(6):1343-8. PubMed PMID: 15161786.

73. Malik R A, Newrick P G, Sharma A K, Jennings A, Ah-See A K, Mayhew T M, Jakubowski J, Boulton A J, Ward J D. Microangiopathy in human diabetic neuropathy: relationship between capillary abnormalities and the severity of neuropathy. Diabetologia. 1989; 32(2):92-102. PubMed PMID: 2721843.

74. Greenman R L, Panasyuk S, Wang X, Lyons T E, Dinh T, Longoria L, Giurini J M, Freeman J, Khaodhiar L, Veves A. Early changes in the skin microcirculation and muscle metabolism of the diabetic foot. Lancet. 2005; 366(9498):1711-7. doi: 10.1016/S0140-6736(05)67696-9. PubMed PMID: 16291064.

75. Dinh T, Veves A. Microcirculation of the diabetic foot. Curr Pharm Des. 2005; 11(18):2301-9. PubMed PMID: 16022669.

76. Cobb J, Claremont D. Noninvasive measurement techniques for monitoring of microvascular function in the diabetic foot. Int J Low Extrem Wounds. 2002; 1(3):161-9. doi: 10.1177/153473460200100303. PubMed PMID: 15871967.

77. Caselli A, Latini V, Lapenna A, Di Carlo S, Pirozzi F, Benvenuto A, Uccioli L. Transcutaneous oxygen tension monitoring after successful revascularization in diabetic patients with ischaemic foot ulcers. Diabet Med. 2005; 22(4):460-5. doi: 10.1111/j.1464-5491.2005.01446.x. PubMed PMID: 15787673.

78. Arsenault K A, McDonald J, Devereaux P J, Thorlund K, Tittley J G, Whitlock R P. The use of transcutaneous oximetry to predict complications of chronic wound healing: a systematic review and meta-analysis. Wound Repair Regen. 2011; 19(6):657-63. doi: 10.1111/j. 1524-475X.2011.00731.x. PubMed PMID: 22092835.

79. Boyko E J, Ahroni J H, Stensel V L, Smith D G, Davignon D R, Pecoraro R E. Predictors of transcutaneous oxygen tension in the lower limbs of diabetic subjects.

80. Ladurner R, Kuper M, Konigsrainer I, Lob S, Wichmann D, Konigsrainer A, Coerper S, Beckert S. Predictive value of routine transcutaneous tissue oxygen tension (tcpO2) measurement for the risk of non-healing and amputation in diabetic foot ulcer patients with non-palpable pedal pulses. Med Sci Monit. 2010; 16(6):CR273-7. PubMed PMID: 20512089.
81. Forsythe R O, Hinchliffe R J. Assessment of foot perfusion in patients with a diabetic foot ulcer. Diabetes Metab Res Rev. 2016; 32 Suppl 1:232-8. doi: 10.1002/dmrr.2756. PubMed PMID: 26813616.
82. Zheng J, Hasting M K, Zhang X, Coggan A, An H, Snozek D, Curci J, Mueller M J. A pilot study of regional perfusion and oxygenation in calf muscles of individuals with diabetes with a noninvasive measure. J Vasc Surg. 2014; 59(2):419-26. doi: 10.1016/j.jvs.2013.07.115. PubMed PMID: 24080129; PMCID: PMC4114721.
83. Zheng J, Hastings M K, Muccigross D, Fan Z, Gao F, Curci J, Hildebolt C F, Mueller M J. Non-contrast MRI perfusion angiosome in diabetic feet. Eur Radiol. 2015; 25(1):99-105. doi: 10.1007/s00330-014-3337-0. PubMed PMID: 25100334.
84. Hastings M K, Mueller M J, Sinacore D R, Strube M J, Crowner B E, Johnson J E, Racette B R. Botulinum toxin effects on gasatrocnemius strength and plantar pressure in diabetics with peripheral neuropathy and forefoot ulceration. Foot Ankle Int. 2012; 33(5):363-70. doi: 10.3113/FAI.2012.0363. PubMed PMID: 22735277; PMCID: PMC3747956.
85. Mueller M J, Tuttle L J, Lemaster J W, Strube M J, McGill J B, Hastings M K, Sinacore D R. Weight-bearing versus nonweight-bearing exercise for persons with diabetes and peripheral neuropathy: a randomized controlled trial. Arch Phys Med Rehabil. 2013; 94(5):829-38. doi: 10.1016/j.apmr.2012.12.015. PubMed PMID: 23276801; PMCID: PMC3637853.
86. Hilton T N, Tuttle L J, Bohnert K L, Mueller M J, Sinacore D R. Excessive adipose tissue infiltration in skeletal muscle in individuals with obesity, diabetes mellitus, and peripheral neuropathy: association with performance and function. Phys Ther. 2008; 88(11): 1336-44. doi: 10.2522/ptj.20080079. PubMed PMID: 18801853; PMCID: PMC2579904.
87. TH I J, Schaper N C, Melai T, Meijer K, Willems P J, Savelberg H H. Lower extremity muscle strength is reduced in people with type 2 diabetes, with and without polyneuropathy, and is associated with impaired mobility and reduced quality of life. Diabetes Res Clin Pract. 2012; 95(3):345-51. doi: 10.1016/j.diabres.2011.10.026. PubMed PMID: 22104262.
88. Park S W, Goodpaster B H, Lee J S, Kuller L H, Boudreau R, de Rekeneire N, Harris T B, Kritchevsky S, Tylavsky F A, Nevitt M, Cho Y W, Newman A B, Health A, Body Composition S. Excessive loss of skeletal muscle mass in older adults with type 2 diabetes. Diabetes Care. 2009; 32(11):1993-7. doi: 10.2337/dc09-0264. PubMed PMID: 19549734; PMCID: PMC2768193.
89. Park S W, Goodpaster B H, Strotmeyer E S, de Rekeneire N, Harris T B, Schwartz A V, Tylavsky F A, Newman A B. Decreased muscle strength and quality in older adults with type 2 diabetes: the health, aging, and body composition study. Diabetes. 2006; 55(6):1813-8. doi: 10.2337/db05-1183. PubMed PMID: 16731847.
90. Bohannon R W, Wang Y C, Gershon R C. Two-minute walk test performance by adults 18 to 85 years: normative values, reliability, and responsiveness. Arch Phys Med Rehabil. 2015; 96(3):472-7. doi: 10.1016/j.apmr.2014.10.006. PubMed PMID: 25450135.
91. Brooks D, Parsons J, Hunter J P, Devlin M, Walker J. The 2-minute walk test as a measure of functional improvement in persons with lower limb amputation. Arch Phys Med Rehabil. 2001; 82(10):1478-83. doi: 10.1053/apmr.2001.25153. PubMed PMID: 11588757.
92. McCommis K S, Goldstein T A, Abendschein D R, Herrero P, Misselwitz B, Gropler R J, Zheng J. Quantification of regional myocardial oxygenation by magnetic resonance imaging: validation with positron emission tomography. Circ Cardiovasc Imaging. 2010; 3(1):41-6. doi: 10.1161/CIRCIMAGING.109.897546. PubMed PMID: 19933371; PMCID: PMC3076677.
93. McCommis K S, Zhang H, Goldstein T A, Misselwitz B, Abendschein D R, Gropler R J, Zheng J. Myocardial blood volume is associated with myocardial oxygen consumption: an experimental study with cardiac magnetic resonance in a canine model. JACC Cardiovasc Imaging. 2009; 2(11):1313-20. doi: 10.1016/j.jcmg.2009.07.010. PubMed PMID: 19909936; PMCID: PMC2796870.
94. Zheng J, An H, Coggan A R, Zhang X, Bashir A, Muccigrosso D, Peterson L R, Gropler R J. Noncontrast skeletal muscle oximetry. Magn Reson Med. 2014; 71(1): 318-25. doi: 10.1002/mrm.24669. PubMed PMID: 23424006; PMCID: PMC3661680.
95. Sadamoto T, Bonde-Petersen F, Suzuki Y. Skeletal muscle tension, flow, pressure, and EMG during sustained isometric contractions in humans. Eur J Appl Physiol Occup Physiol. 1983; 51(3):395-408. PubMed PMID: 6685038.
96. Bauer T A, Reusch J E, Levi M, Regensteiner J G. Skeletal muscle deoxygenation after the onset of moderate exercise suggests slowed microvascular blood flow kinetics in type 2 diabetes. Diabetes Care. 2007; 30(11): 2880-5. doi: 10.2337/dc07-0843. PubMed PMID: 17675540.
97. Soontornniyomkij V, Kesby J P, Morgan E E, Bischoff-Grethe A, Minassian A, Brown G G, Grant I, Translational Methamphetamine ARCG. Effects of HIV and Methamphetamine on Brain and Behavior: Evidence from Human Studies and Animal Models. J Neuroimmune Pharmacol. 2016; 11(3):495-510. doi: 10.1007/s11481-016-9699-0. PubMed PMID: 27484318; PMCID: PMC4985024.
98. Nahid P, Saukkonen J, Mac Kenzie W R, Johnson J L, Phillips P P, Andersen J, Bliven-Sizemore E, Belisle J T, Boom W H, Luetkemeyer A, Campbell T B, Eisenach K D, Hafner R, Lennox J L, Makhene M, Swindells S, Villarino M E, Weiner M, Benson C, Burman W, National Institutes of H, Centers for Disease C, Prevention. CDC/NIH Workshop. Tuberculosis biomarker and surrogate endpoint research roadmap. Am J Respir Crit Care Med. 2011; 184(8):972-9. doi: 10.1164/rccm.201105-0827WS. PubMed PMID: 21737585; PMCID: PMC3208659.
99. Stegeman S, Amankwah E, Klein K, O'Mara T A, Kim D, Lin H Y, Permuth-Wey J, Sellers T A, Srinivasan S, Eeles R, Easton D, Kote-Jarai Z, Amin Al Olama A, Benlloch S, Muir K, Giles G G, Wiklund F, Gronberg H, Haiman C A, Schleutker J, Nordestgaard B G, Travis R C, Neal D, Pharoah P, Khaw K T, Stanford J L, Blot W J, Thibodeau S, Maier C, Kibel A S, Cybulski C, Cannon-Albright L, Brenner H, Kaneva R, Teixeira M R, Consortium P, Australian Prostate Cancer B, Spurdle A B, Clements J A, Park J Y, Batra J. A Large-Scale Analysis of Genetic Variants within Putative miRNA Binding Sites in Prostate Cancer. Cancer Discov. 2015; 5(4):368-79. doi: 10.1158/2159-8290.CD-14-1057. PubMed PMID: 25691096; PMCID: PMC4390388.

100. Kirchhoff T, Gaudet M M, Antoniou A C, McGuffog L, Humphreys M K, Dunning A M, Bojesen S E, Nordestgaard B G, Flyger H, Kang D, Yoo K Y, Noh D Y, Ahn S H, Dork T, Schurmann P, Karstens J H, Hillemanns P, Couch F J, Olson J, Vachon C, Wang X, Cox A, Brock I, Elliott G, Reed M W, Burwinkel B, Meindl A, Brauch H, Hamann U, Ko Y D, Network G, Broeks A, Schmidt M K, Van't Veer L J, Braaf L M, Johnson N, Fletcher O, Gibson L, Peto J, Turnbull C, Seal S, Renwick A, Rahman N, Wu P E, Yu J C, Hsiung C N, Shen C Y, Southey M C, Hopper J L, Hammet F, Van Dorpe T, Dieudonne A S, Hatse S, Lambrechts D, Andrulis I L, Bogdanova N, Antonenkova N, Rogov J I, Prokofieva D, Bermisheva M, Khusnutdinova E, van Asperen C J, Tollenaar R A, Hooning M J, Devilee P, Margolin S, Lindblom A, Milne R L, Arias J I, Zamora M P, Benitez J, Severi G, Baglietto L, Giles G G, kConFab, Group A S, Spurdle A B, Beesley J, Chen X, Holland H, Healey S, Wang-Gohrke S, Chang-Claude J, Mannermaa A, Kosma V M, Kauppinen J, Kataja V, Agnarsson B A, Caligo M A, Godwin A K, Nevanlinna H, Heikkinen T, Fredericksen Z, Lindor N, Nathanson K L, Domchek S M, Swe B, Loman N, Karlsson P, Stenmark Askmalm M, Melin B, von Wachenfeldt A, Hebon, Hogervorst F B, Verheus M, Rookus M A, Seynaeve C, Oldenburg R A, Ligtenberg M J, Ausems M G, Aalfs C M, Gille H J, Wijnen J T, Gomez Garcia E B, Embrace, Peock S, Cook M, Oliver C T, Frost D, Luccarini C, Pichert G, Davidson R, Chu C, Eccles D, Ong K R, Cook J, Douglas F, Hodgson S, Evans D G, Eeles R, Gold B, Pharoah P D, Offit K, Chenevix-Trench G, Easton D F, Bcac/Cimba. Breast cancer risk and 6q22.33: combined results from Breast Cancer Association Consortium and Consortium of Investigators on Modifiers of BRCA1/2. PLoS One. 2012; 7(6):e35706. doi: 10.1371/journal.pone.0035706. PubMed PMID: 22768030; PMCID: PMC3387216.

What is claimed is:

1. A method of detecting circulating Fatty Acid Synthase (FAS) enzymatic activity in a subject who has or is suspected of having a cardiovascular-related disease, disorder, or condition, comprising:
providing a serum or plasma sample from the subject; and
detecting a level of circulating FAS enzymatic activity using a nicotinamide adenine dinucleotide phosphate hydrogen (NADPH) depletion assay in the serum or plasma sample,
wherein the serum or plasma is in an amount sufficient for the circulating FAS enzymatic activity level to be detected in a NADPH depletion assay.

2. The method of claim 1, wherein the subject has diabetes.

3. The method of claim 1, comprising treating the subject for a foot wound or for a cardiovascular-related disease, disorder, or condition.

4. The method of claim 3, wherein the cardiovascular-related disease, disorder, or condition comprises a foot wound, carotid occlusive disease, atherosclerotic disease, atherosclerosis, peripheral artery disease (PAD), or carotid artery stenosis.

5. The method of claim 1, wherein an elevated level of circulating FAS enzymatic activity in serum of the subjects indicates the subject has type 2 diabetes, increased probability of scoring higher on a Diabetes Complications Severity Index (DCSI), or increased probability of having peripheral arterial disease (PAD) compared to a control.

6. The method of claim 5, wherein an increased levels of circulating FAS enzymatic activity indicates increased levels of serum low-density lipoprotein (LDL) particles or increased levels of LDL particles deposited in high amounts in peripheral arterial plaque compared to a control.

7. A method of treating a subject with a foot wound or a cardiovascular-related disease, disorder, or condition, comprising:
measuring a level of circulating FAS enzymatic activity in the serum or plasma according to claim 1 obtained from a subject; and
treating the subject having the foot wound or the cardiovascular-related disease, disorder, or condition with a therapeutic agent if the subject has an elevated circulating FAS enzymatic activity compared to a control.

8. The method of claim 7, wherein the subject has a cardiovascular-related disease, disorder, or condition and is treated with a cardiac therapeutic agent if the subject has an elevated circulating FAS enzymatic activity compared to a control.

9. The method of claim 7, wherein the subject has diabetes.

10. The method of claim 7, wherein a first circulating FAS enzymatic activity is measured and a second circulating FAS enzymatic activity is measured.

11. The method of claim 10, wherein
(i) an elevated first circulating FAS enzymatic activity compared to the second circulating FAS enzymatic activity indicates foot wound healing;
(ii) an elevated second circulating FAS enzymatic activity or compared to a first circulating FAS enzymatic activity indicates foot wound progression; or
(iii) an elevated second circulating FAS enzymatic activity compared to a first circulating FAS enzymatic activity indicates an increase in disease severity or disease progression.

12. The method of claim 7, wherein the subject has a foot wound, atherosclerotic disease, or peripheral artery disease (PAD).

13. The method of claim 11, wherein the therapeutic agent is effective if the second circulating FAS enzymatic activity is reduced compared to the first circulating FAS enzymatic activity.

14. The method of claim 7, wherein the therapeutic agent is a vasodilator.

15. A method of diagnosing a cardiovascular-related disease, disorder, or condition comprising:
providing a serum or plasma sample from a subject suspected of having a cardiovascular-related disease, disorder, or condition; detecting a circulating FAS enzymatic activity level using a NADPH depletion assay in the serum or plasma sample; and
comparing the circulating FAS enzymatic activity level of the subject and a control sample;
wherein,
the subject is diagnosed with a cardiovascular-related disease, disorder, or condition if the circulating FAS enzymatic activity level in the subject is elevated compared to the circulating FAS enzymatic activity level in a control sample; and
the serum or plasma is in an amount sufficient for the circulating FAS enzymatic activity level to be detected in a NADPH depletion assay.

16. The method of claim 15, further comprising treating a subject for a cardiovascular-related disease, disorder, or condition.

17. The method of claim 15, wherein the cardiovascular-related disease, disorder, or condition comprises a foot wound, carotid occlusive disease, atherosclerotic disease, atherosclerosis, peripheral artery disease (PAD), or carotid artery stenosis.

18. The method claim 15, wherein the subject has diabetes.

19. The method of claim 15, wherein the control subject does not have a cardiovascular-related disease or an arterial occlusive disease.

20. The method of claim 1, wherein the cardiovascular-related disease, disorder, or condition is peripheral artery disease (PAD).

21. The method of claim 1, wherein the subject has a cardiovascular-related disease and diabetes and does not have cancer.

22. The method of claim 21, wherein the cardiovascular-related disease is peripheral artery disease (PAD).

23. The method of claim 7, wherein the therapeutic agent is cilostazol.

\* \* \* \* \*